US012385911B2

(12) United States Patent
Leonard et al.

(10) Patent No.: US 12,385,911 B2
(45) Date of Patent: *Aug. 12, 2025

(54) ENGINEERED RED BLOOD CELL-BASED BIOSENSORS

(71) Applicant: Northwestern University, Evanston, IL (US)

(72) Inventors: Joshua N. Leonard, Wilmette, IL (US); Kelly A. Schwarz, Evanston, IL (US); Taylor B. Dolberg, Evanston, IL (US)

(73) Assignee: Northwestern University, Evanston, IL (US)

( * ) Notice: Subject to any disclaimer, the term of this patent is extended or adjusted under 35 U.S.C. 154(b) by 1332 days.

This patent is subject to a terminal disclaimer.

(21) Appl. No.: 16/995,194

(22) Filed: Aug. 17, 2020

(65) Prior Publication Data

US 2020/0393458 A1    Dec. 17, 2020

Related U.S. Application Data

(63) Continuation of application No. 15/908,077, filed on Feb. 28, 2018, now Pat. No. 10,753,930.

(60) Provisional application No. 62/464,754, filed on Feb. 28, 2017.

(51) Int. Cl.
| | |
|---|---|
| *G01N 33/555* | (2006.01) |
| *C12N 5/078* | (2010.01) |
| *G01N 21/64* | (2006.01) |
| *G01N 33/566* | (2006.01) |
| *G01N 33/80* | (2006.01) |

(52) U.S. Cl.
CPC ......... *G01N 33/555* (2013.01); *C12N 5/0641* (2013.01); *G01N 21/6428* (2013.01); *G01N 33/566* (2013.01); *C12N 2510/00* (2013.01); *G01N 33/80* (2013.01)

(58) Field of Classification Search
None
See application file for complete search history.

(56) References Cited

U.S. PATENT DOCUMENTS

| | | | |
|---|---|---|---|
| 9,732,392 B2 | 8/2017 | Leonard | |
| 10,753,930 B2 * | 8/2020 | Leonard | G01N 21/6428 |

OTHER PUBLICATIONS

Wehr et al., "Split protein biosensor assays in molecular pharmacological studies" 21(3) Drug Discovery Today 415-429 (Year: 2016).*

Daringer, N; Dudek, R; Schwarz, K; Leonard, J. A Modular Extracellular Sensor Architecture for Engineering Mammalian Cell-based Devices. ACS Synthetic Biology, 3 (12), 892-902 (2014).
Dixon, A. S., et al. Nantou Complementation Reporter Optimized for Accurate Measurement of Protein Interactions in Cells. ACS Chem Biol 11(2) 400-408, doi: DOI 10.1021/acschembio.5b00753 (2016).
Filonov, G.S., Verkhusha, V. V. A Near-Infrared BiFC Reporter for In Vivo Imaging of Protein-Protein Interactions. Chemistry & Biology 20, 1078-1086 (2013).
Ghosh, I., Hamilton, A. D. & Regan, L. Antiparallel leucine zipper-directed protein reassembly: Application to the green fluorescent protein. J Am Chem Soc 122, 5658-5659, doi:Doi 10.1021/Ja994421w (2000).
Lemmon, M. A., et al. Glycophorin A dimerization is driven by specific interactions between transmembrane alpha-helices. J Biol Chem 267(11): 7683-7689 (1992).
Li, E., et al. Transmembrane helix dimerization: beyond the search for sequence motifs. Biochim Biophys Acta 1818(2): 183-193 (2012).
Shi, J. H. et al. Engineered red blood cells as carriers for systemic delivery of a wide array of functional probes. Proceedings of the National Academy of Sciences of the United States of America 111, 10131-10136, doi:DOI 10.1073/pnas.1409861111 (2014).
Wang et al., "Recent Progress in Strategies for the Creation of Protein-Based Fluorescent Biosensors," ChemBioChem, 2009, 10:2560-2577.

* cited by examiner

*Primary Examiner* — Nancy J Leith
(74) *Attorney, Agent, or Firm* — Foley & Lardner LLP

(57) ABSTRACT

Disclosed are systems and methods for detecting extracellular ligands. The disclosed systems and method for detecting extracellular ligands typically comprise or utilize engineered red blood cells (eRBCs) that comprises modular extracellular sensors. The eRBCs may comprise: (i) a first exogenous extracellular sensor; the first extracellular sensor comprising: a) a ligand binding domain, b) a transmembrane domain, and c) a first fragment of a functional protein, and (ii) a second exogenous extracellular sensor; the second extracellular sensor comprising: a) a ligand binding domain, b) a transmembrane domain, and c) a second fragment of the functional protein. In the eRBCs, the ligand binding domain of the first exogenous sensor and the ligand binding domain of the second exogenous sensor bind to the same ligand to form a tertiary complex, and the first fragment of the functional protein and the second fragment of the functional protein interact in the tertiary complex to reconstitute functional activity of the functional protein. Suitable functional proteins for the disclosed eRBCs may include fluorescent proteins that emit fluorescence when the ligand binding domain of the first exogenous sensor and the ligand binding domain of the second exogenous sensor bind to the same ligand, and enzymatic proteins that exhibit enzymatic activity when ligand binding domain of the first exogenous sensor and the ligand binding domain of the second exogenous sensor bind to the same ligand.

19 Claims, 13 Drawing Sheets

Specification includes a Sequence Listing.

ENGINEERED RED BLOOD CELL-BASED BIOSENSORS

CROSS-REFERENCE TO RELATED PATENT APPLICATIONS

The present application is a Continuation of U.S. application Ser. No. 15/908,077, filed Feb. 28, 2018, which claims the benefit of priority under 35 U.S.C. § 119(e) to U.S. Provisional Application No. 62/464,754, filed on Feb. 28, 2017, the content of which is incorporated herein by reference in its entirety.

STATEMENT REGARDING FEDERALLY SPONSORED RESEARCH OR DEVELOPMENT

This invention was made with government support under 11-23-CCM-DT-FP-008 awarded by The Defense Advanced Research Projects Agency (DARPA). The government has certain rights in the invention

SEQUENCE LISTING

The instant application contains a Sequence Listing which has been submitted in TXT format and is hereby incorporated by reference in its entirety. Said TXT copy, created on Feb. 20, 2025, is named 121384-0147 SL.txt and is 10,151 bytes.

BACKGROUND

The present invention provides modular extracellular sensors, nucleic acids encoding such sensors, cells expressing such sensors, systems and methods of employing such sensors and cells for detecting extracellular ligands. In particular, the invention relates to red blood cells that have been engineered to express modular extracellular sensors for detecting extracellular ligands.

SUMMARY

Disclosed are systems and methods for detecting extracellular ligands. The disclosed systems and method for detecting extracellular ligands typically comprise or utilize engineered red blood cells (eRBCs) that comprises modular extracellular sensors. The eRBCs may comprise: (i) a first exogenous extracellular sensor; the first extracellular sensor comprising: a) an extracellular ligand binding domain or a portion thereof, b) a transmembrane domain, and c) a first fragment of a functional protein, and (ii) a second exogenous extracellular sensor; the second extracellular sensor comprising: a) an extracellular ligand binding domain or a portion thereof, b) a transmembrane domain, and c) a second fragment of the functional protein. In the eRBCs, the extracellular ligand binding domain of the first exogenous sensor and the ligand binding domain of the second exogenous sensor bind to a ligand to form a ternary complex (which may be the same ligand), and the first fragment of the functional protein and the second fragment of the functional protein interact in the ternary complex to reconstitute functional activity of the functional protein.

The first exogenous sensor and/or the second exogenous sensor may be derived, prepared, and/or engineered from native membrane proteins of RBCs or portions or fragments thereof. For example, the first exogenous sensor and/or the second exogenous sensor may be derived, prepared, and/or engineered from a portion of a native membrane protein of a RBC comprising at least the transmembrane portion to which is fused a ligand binding domain at the extracellular terminus and a functional protein (or a portion of a functional protein) at the intracellular terminus. The transmembrane portion further may be mutated in order to prevent homodimerization of the transmembrane portion with another transmembrane portion, for example, where the native membrane protein form a homodimer in native conditions.

Suitable functional proteins for the disclosed eRBCs may include fluorescent proteins that emit fluorescence when the ligand binding domain of the first exogenous sensor and the ligand binding domain of the second exogenous sensor bind to the same ligand, and enzymatic proteins that exhibit enzymatic activity when ligand binding domain of the first exogenous sensor and the ligand binding domain of the second exogenous sensor bind to the same ligand. Substrates for the enzymatic proteins may include substrates that are luminescent after they are metabolized by the enzymatic protein.

DETAILED DESCRIPTION

Figure 1:
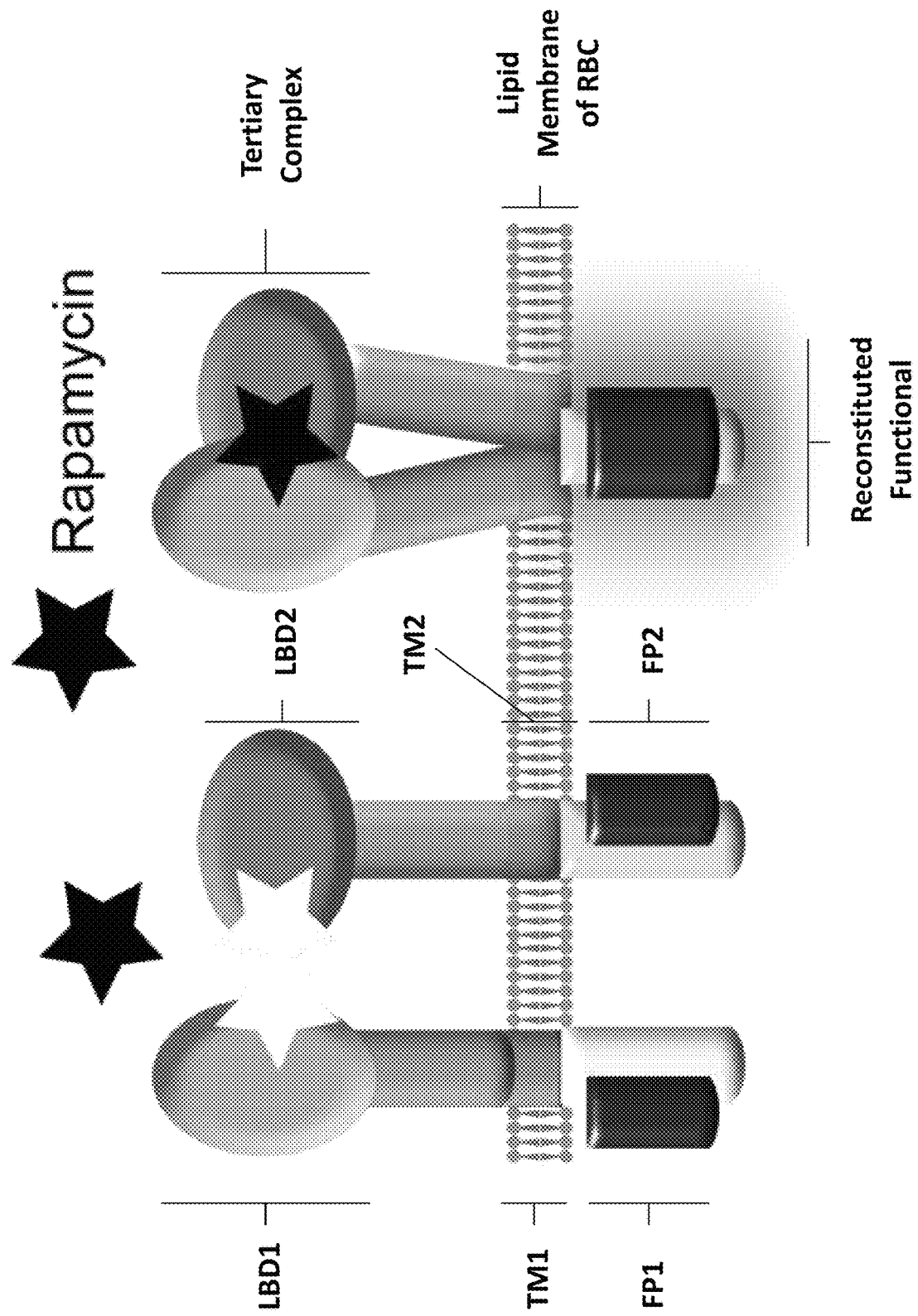
FIG. 1: Proposed mechanism of protein-based biosensors.

The present invention is described herein using several definitions, as set forth below and throughout the application.

Unless otherwise specified or indicated by context, the terms "a", "an", and "the" mean "one or more." For example, "a receptor," "ligand," and "complex" should be interpreted to mean "one or more receptors," "ligands," and "complexes," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ?10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The disclosed technology relates to "extracellular sensors." As disclosed herein, an "extracellular sensor" is a molecule or a system of molecules that can be used to bind to a ligand and provide a detectable response based on binding the ligand. Extracellular sensors are disclosed in the art. (See, e.g., Daringer et al., "Modular Extracellular Sensor Architecture for Engineering Mammalian Cell-based Devices," Nichole M. Daringer, Rachel M. Dudek, Kelly A. Schwarz, and Josh N. Leonard, ACS Synth. Biol. 2014, 3, 892-902, published Feb. 25, 2014; WO 2013/022739, published on Feb. 14, 2013; and U.S. Publication No. 2014-0234851; the contents of which are incorporated herein by reference in their entireties).

The disclosed extracellular sensors typically include a ligand-binding domain of a ligand-binding protein. As contemplated herein, a "ligand-binding protein" is a macromolecule, typically a protein, which binds to a ligand. For example, a ligand-binding protein may include a receptor for a ligand or a portion of a receptor for a ligand, for example, where the receptor is a membrane protein and the ligand-binding protein comprises the extracellular portion of the receptor that binds an extracellular ligand. A suitable ligand for the ligand-binding domains of the disclosed extracellular sensors may include more than one binding site for a ligand-binding protein. As such, a suitable ligand can bind more than one ligand-binding domain of one or more extracellular sensors as contemplated herein, and as such, a suitable ligand may form a ternary or high order complex with two or more extracellular sensors.

The disclosed exogenous sensors may be utilized for sensing an extracellular ligand and providing a molecular signal when the ligand is sensed. Suitable molecular signals may be generated via so-called "bimolecular complementation" that occurs between two or more exogenous sensors (or between portions of two or more exogenous sensors) when the ligand is sensed. "Bimolecular complementation" is known in the art, for example, bimolecular fluorescence complementation and split enzyme complementation or protein-fragment complementation are known in the art. (See Kodama et al., "Bimolecular fluorescence complementation (BiFC): A 5-year update and future perspectives, BioTechniques, Vol. 53, No. 5, November 2012, pp. 285-298. See also Remy et al., "Application of protein-fragment complementation assays in cell biology," BioTechniques, Vol. 42, No. 2, 2007, pages 137-145; and Azad et al., "Split-luciferase complementary assay: Applications, recent developments, and future perspectives," Anal. and Bioanal. Chem 406(23) 2014, pages 5541-5560; the contents of which are incorporated herein by reference in their entireties).

Reference is made herein to nucleic acid and nucleic acid sequences. The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

Reference also is made herein to peptides, polypeptides, proteins and compositions comprising peptides, polypeptides, and proteins. As used herein, a polypeptide and/or protein is defined as a polymer of amino acids, typically of length >100 amino acids (Garrett & Grisham, Biochemistry, 2nd edition, 1999, Brooks/Cole, 110). A peptide is defined as a short polymer of amino acids, of a length typically of 20 or less amino acids, and more typically of a length of 12 or less amino acids (Garrett & Grisham, Biochemistry, 2nd edition, 1999, Brooks/Cole, 110).

As disclosed herein, exemplary peptides, polypeptides, proteins may comprise, consist essentially of, or consist of any reference amino acid sequence disclosed herein, or variants of the peptides, polypeptides, and proteins may comprise, consist essentially of, or consist of an amino acid sequence having at least about 80%, 90%, 95%, 96%, 97%, 98%, or 99% sequence identity to any amino acid sequence disclosed or contemplated herein. Variant peptides, polypeptides, and proteins may include peptides, polypeptides, and proteins having one or more amino acid substitutions, deletions, additions and/or amino acid insertions relative to a reference peptide, polypeptide, or protein. Also disclosed are nucleic acid molecules that encode the disclosed peptides, polypeptides, and proteins (e.g., polynucleotides that encode any of the peptides, polypeptides, and proteins disclosed herein and variants thereof).

The term "amino acid," includes but is not limited to amino acids contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, ?-alanine, ?-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

The amino acid sequences contemplated herein may include conservative amino acid substitutions relative to a reference amino acid sequence. For example, a variant peptides, polypeptides, and proteins as contemplated herein may include conservative amino acid substitutions relative to an amino acid sequence of a reference peptide, polypeptide, or protein. "Conservative amino acid substitutions" are those substitutions that are predicted to interfere least with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

| Table of Conservative Amino Acid Substitutions | |
|---|---|
| Original Residue | Conservative Substitution |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |

-continued

| Table of Conservative Amino Acid Substitutions | |
|---|---|
| Original Residue | Conservative Substitution |
| Ser | Cys, Thr |
| Thr | Ser, Val |
| Trp | Phe, Tyr |
| Tyr | His, Phe, Trp |
| Val | Ile, Leu, Thr |

"Non-conservative amino acid substitutions" are those substitutions that are predicted to interfere most with the properties of the reference peptide, polypeptide, or protein. For example, a non-conservative amino acid substitution might replace a basic amino acid at physiological pH such as Arg, His, or Lys, with a non-basic or acidic amino acid at physiological pH such as Asp or Glu. A non-conservative amino acid substitution might replace a non-polar amino acid at physiological pH such as Ala, Gly, Ile, Leu, Phe, or Val, with a polar amino acid at physiological pH such as Arg, Asp, Glu, His, or Lys.

Variants comprising deletions relative to a reference amino acid sequence or nucleotide sequence are contemplated herein. A "deletion" refers to a change in a reference amino acid sequence that results in the absence of one or more amino acid residues. A deletion removes at least 1, 2, 3, 4, 5, 10, 20, 50, 100, or 200 amino acids residues or a range of amino acid residues bounded by any of these values (e.g., a deletion of 5-10 amino acids). A deletion may include an internal deletion or a terminal deletion (e.g., an N-terminal truncation or a C-terminal truncation of a reference polypeptide). A "variant" of a reference polypeptide sequence may include a deletion relative to the reference polypeptide sequence (e.g., relative to any of SEQ ID NOs:1-3).

The words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues or a range of amino acid residues bounded by any of these values (e.g., an insertion or addition of 5-10 amino acids). A "variant" of a reference polypeptide sequence may include an insertion or addition relative to the reference polypeptide sequence (e.g., relative to any of SEQ ID NOs:1-3).

A "fusion polypeptide" refers to a polypeptide comprising at the N-terminus, the C-terminus, or at both termini of its amino acid sequence a heterologous amino acid sequence, for example, a heterologous amino acid sequence that extends the half-life of the fusion polypeptide in serum. A "variant" of a reference polypeptide sequence may include a fusion polypeptide comprising the reference polypeptide.

A "fragment" is a portion of an amino acid sequence which is identical in sequence to but shorter in length than a reference sequence (e.g., a fragment of any of SEQ ID NOs:1-3). A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, or 500 contiguous amino acid residues of a reference polypeptide; or a fragment may comprise no more than 5, 10, 15, 20, 25, 30, 40, 50, 60, 70, 80, 90, 100, 150, 250, or 500 contiguous amino acid residues of a reference polypeptide; or a fragment may comprise a range of contiguous amino acid residues of a reference polypeptide bounded by any of these values (e.g., 40-80 contiguous amino acid residues). Fragments may be preferentially selected from certain regions of a molecule. The term "at least a fragment" encompasses the full length polypeptide. A "variant" of a reference polypeptide sequence may include a fragment of the reference polypeptide sequence.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 100, at least 150, at least 200, at least 250, at least 300, at least 350, at least 400, at least 450, at least 500, at least 550, at least 600, at least 650, or at least 700 contiguous amino acid residues; or a fragment of no more than 15, 20, 30, 40, 50, 100, 150, 200, 250, 300, 350, 400, 450, 500, 550, 600, 650, or 700 amino acid residues; or over a range bounded by any of these values (e.g., a range of 500-600 amino acid residues) Such lengths are exemplary only, and it is understood that any fragment length supported by the sequences shown herein, in the tables, figures or Sequence Listing, may be used to describe a length over which percentage identity may be measured.

In some embodiments, a "variant" of a particular polypeptide sequence may be defined as a polypeptide sequence having at least 20% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides, or range of percentage identity bounded by any of these values (e.g., range of percentage identity of 80-99%).

The disclosed fusion polypeptides may comprise a amino acid sequence fused directly to a heterologous amino acid sequence or fused indirectly via a linker sequence. Suitable linker sequences may include amino acid sequences of 5, 6, 7, 8, 9, 10, 11, 12, 13, 14, or 15 amino acids or more, or a range bounded by any of these values (e.g., a linker of 5-25 amino acids). In some embodiments, the linker sequence comprises only glycine and serine residues.

Fusion polypeptide disclosed herein may include an amino acid tag sequence, for example, which may be utilized for purifying and or identifying the fusion polypeptide. Suitable amino acid tag sequences may include, but are not limited to, histidine tag sequences comprising 5-10 histidine residues.

A variant polypeptide may have substantially the same functional activity as a reference polypeptide. For example, a variant polypeptide may exhibit or more biological activities associated with binding a ligand, exhibiting fluorescence, and/or enzymatic activity.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Percent identity may be measured over the length of an entire defined polynucleotide sequence or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length may be used to describe a length over which percentage identity may be measured.

A "full length" polynucleotide sequence of a gene is one containing at least a translation initiation codon (e.g., methionine) followed by an open reading frame and a translation termination codon. A "full length" polynucleotide sequence encodes a "full length" polypeptide sequence.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polynucleotide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polynucleotide.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, $2^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

"Transfection" and "transformation" describe a process by which exogenous DNA is introduced into a recipient cell. Transfection and transformation may occur under natural or artificial conditions according to various methods well known in the art, and may rely on any known method for the insertion of foreign nucleic acid sequences into a prokaryotic or eukaryotic host cell. The method for transfection or transformation is selected based on the type of host cell being transformed and may include, but is not limited to, bacteriophage or viral infection, electroporation, heat shock, lipofection, and particle bombardment. The terms "transfected cells" and "transformed cells" include stably transfected cells or transformed cells in which the inserted DNA is capable of replication either as an autonomously replicating plasmid or as part of the host chromosome, as well as transiently transfected cells or transformed cells which express the inserted DNA or RNA for limited periods of time.

The polynucleotide sequences contemplated herein may be present in expression cassettes and/or expression vectors (e.g., an expression vector comprising an expression cassette). For example, the vectors may comprise a polynucleotide encoding an ORF of a recombinant protein (e.g., an exogenous sensor as disclosed herein). The polynucleotide present in the vector may be operably linked to a promoter (e.g., a eukaryotic promoter or prokaryotic promoter). "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. For example, a heterologous promoter for a LAMP may include a eukaryotic promoter or a prokaryotic promoter that is not the native, endogenous promoter for the LAMP.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, an "expression cassette" minimally refers to a recombinant polynucleotide comprising a promoter operably linked to a recombinant coding sequence. An expression cassette may be present in a vector (e.g., an episomal vector which is transfected into a cell and remains episomal and/or which recombines into the genome of the cell). A vector may include one or more expression cassettes which express one or more coding sequences (e.g., one or more coding sequences for sensors as disclosed herein).

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refer to a recombinant nucleic acid that has been engineered to express a heterologous polypeptide (e.g., the fusion proteins disclosed herein). The recombinant nucleic acid typically includes cis-acting elements for expression of the heterologous polypeptide.

Any of the conventional vectors used for expression in eukaryotic cells may be used for directly introducing DNA into a subject. Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter, SV40 later promoter, metallothionein promoter, human cytomegalovirus promoter, murine mammary tumor virus promoter, and Rous sarcoma virus promoter. Expression vectors as contemplated herein may include eukaryotic or prokaryotic control sequences that modulate expression of a heterologous protein (e.g. the fusion protein disclosed herein). Prokaryotic expression control sequences may include constitutive or inducible promoters (e.g., T3, T7, Lac, trp, or phoA), ribosome binding sites, or transcription terminators.

The vectors contemplated herein may be introduced and propagated in a prokaryote, which may be used to amplify copies of a vector to be introduced into a eukaryotic cell or as an intermediate vector in the production of a vector to be introduced into a eukaryotic cell (e.g. amplifying a plasmid as part of a viral vector packaging system). A prokaryote may be used to amplify copies of a vector.

The presently disclosed methods may include delivering one or more polynucleotides, such as or one or more vectors as described herein, one or more transcripts thereof, and/or one or proteins transcribed therefrom, to a host cell. Further contemplated are host cells produced by such methods, and organisms (such as animals, plants, or fungi) comprising or produced from such cells. The disclosed extracellular vesicles may be prepared by introducing vectors that express mRNA encoding a fusion protein as contemplated herein. Conventional viral and non-viral based gene transfer methods can be used to introduce nucleic acids in mammalian cells or target tissues. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell.

In the methods contemplated herein, a host cell may be transiently or non-transiently transfected (i.e., stably transfected) with one or more vectors described herein. In some embodiments, a cell is transfected as it naturally occurs in a subject (i.e., in situ). In some embodiments, a cell that is transfected is taken from a subject (i.e., explanted). In some embodiments, the cell is derived from cells taken from a subject, such as a cell line. Suitable cells may include stem cells (e.g., embryonic stem cells and pluripotent stem cells). A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors, or transfection with RNA), and modified through the activity of a complex, in order to establish a new cell line comprising cells containing the modification but lacking any other exogenous sequence.

A "composition comprising a given polypeptide" and a "composition comprising a given polynucleotide" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

The disclosed sensors may include a protease cleavage sequence and/or a cognate protease that recognizes and cleaves the protease cleavage sequence. The sensors are not limited to any particular protease or corresponding protease cleavage site. In some embodiments, the protease and cleavage site are from a virus. For example, in certain embodiments, the protease and protease cleavage site are from a virus selected from: tobacco etch virus (TEV), a chymotrypsin-like serine protease and corresponding cleavage sites, alphavirus proteases and cleavage sites, Hepatitis C virus proteases (e.g., N S3 proteases) and corresponding cleavage sites, chymotrypsin-like cysteine proteases and corresponding cleavage sites, papain-like cysteine proteases and cleavage sites, picornavirus leader proteases and cleavage sites, HIV proteases and cleavage sites, Herpesvirus proteases and cleavage sites, and adenovirus proteases and cleavage sites (see, Tong, Chem. Rev. 2002, 102, 4609-4626, herein incorporated by reference in its entirety). In particular embodiments, the proteases and cleavage sites are bacterial in original, such as, for example, from *Streptomyces griseus* protease A (SGPA), SGPB, and alpha-lytic protease and corresponding cleavage sites. In some embodiments, the proteases and cleavage sites are mammalian. For example, the proteases could be one of the five major classes of proteases known in mammals which include serine proteases, cycteine proteases, metallo proteases, aspartic proteases, and thereonine proteases (see, e.g., Turk et al., The EMBO Journal, 2012, 31, 1630-1643; Lopez-Otin and Overall, 2002, Nat. Rev. Mol. Cell Biol., 2:509-519; Overall and Blobel, 2007, Nat. Rev. Mol. Cell Biol., 8: 245-257; and Lopez-Otin and Bond, 2008, J. Biol. Chem., 283:30422-30437, all of which are herein incorporated in their entireties by references.

The disclosed subject matter relates to engineered red blood cells (eRBCs) which interchangeably may be referred to as red blood corpuscles, haematids, erthyroid cells, or erythrocytes. The disclosed eRBCs typically include recombinant membrane proteins for detecting an extracellular ligand and generating a signal if the extracellular ligand is detected (i.e., recombinant exogenous sensors). The disclosed exogenous sensors may be prepared from native and/or non-native proteins of RBCs.

The disclosed eRBCs are anucleatic (i.e., lack a nucleus) and may be prepared from precursor RBCs (e.g., by inducing precursor RBCs to differentiate to RBCs). Precursor RBCs may include, but are not limited to, hemocytoblasts, multipotent heatopoietic stem cells, common myeloid progenitors, multipotent stem cells, unipotent stem cells, pronormoblasts, proerythroblasts, rubriblasts, normoblasts, erythroblasts, polychromatophilic normoblasts, intermediate normoblasts, orthochromatic normoblasts, and/or late normoblasts. The disclosed eRBCs may be prepared by transfected precursor RBCs with expression cassettes and/or expression vectors for expressing biosensors as disclosed herein, and subsequently inducing the transfected precursor RBCs to differentiate to RBCs, thereby obtaining the disclosed eRBCs. The transfected precursor RBCs may be induced to differentiate by methods known in the art including contacting the transfected precursor RBCs and/or culturing the transfected precursor RBCs with differentiation factors (e.g., hormones and/or growth factors).

In some embodiments, the recombinant exogenous sensors may be derived, prepared, or engineered from native membrane proteins of RBCs or portions or fragments of membrane proteins of RBCs. Membrane proteins of RBCs suitable for deriving, preparing, and/or engineering the disclosed sensors may include, but are not limited to glycophorins (e.g., glycophorin A (GPA or GYPA), glycophorin B (GPB or GYPB), glycophorin C (GPC or GYPC), and/or glycophorin E (GPE or GYPE)); Band 3 (major anion transporter); Aquaporin 1 (water transporter); Glut1 (glucose and L-dehydroascorbic acid transporter); Kidd antigen protein (urea transporter); RhAG (gas transporter); $Na^+/K^+$—ATPase; $Ca^{2+}$—ATPase; $Na^+$—$Cl^-$—cotransporter; $Na^+$ $K^+2Cl$—cotransporter; Na—H exchanger; K—Cl—cotransporter; Gardos channel; ICAM-4; BCAM; Kell antigen (XK); RHD/RhCE; Duffy protein; Adducin; and/or Dematin. In some embodiments, the native membrane protein from which the disclosed recombinant extracellular censors are derived, prepared, and/or engineered is a type I membrane protein (i.e., single pass membrane protein with an extracellular N-terminus and an intracellular C-terminus such as GPA) and/or a type II membrane protein (i.e., single pass membrane protein with an extracellular C-terminus and an intracellular N-terminus such as Kell).

The disclosed exogenous sensors include one or more recombinant membrane proteins. In some embodiments, the disclosed exogenous sensors may include two recombinant membrane proteins which are fusion proteins comprising a membrane protein of a RBC or a portion or fragment thereof. In some embodiments, the fusion proteins may comprise a membrane protein of a RBC or a portion or fragment thereof to which a ligand binding domain has been fused at the N-terminus (i.e., $N_{ter}$-(ligand binding domain)-(RBC membrane protein)-$C_{ter}$) or at the C-terminus (i.e., $N_{ter}$-(RBC membrane protein)-(ligand binding domain)-$C_{ter}$). Further, the fusion proteins may comprise a membrane protein of a RBC or a portion or fragment thereof to which a functional protein has been fused at the N-terminus (i.e., $N_{ter}$-(ligand binding domain)-(RBC membrane protein)-(functional protein)-$C_{ter}$) or at the C-terminus (i.e., $N_{ter}$-(functional protein)-(RBC membrane protein)-(ligand binding domain)-$C_{ter}$). A first fusion protein may comprise a non-functional portion of a functional protein, and a second fusion protein may comprise a second non-functional portion of a functional protein such that when the first fusion protein and the second fusion protein bind the ligand for the ligand binding domain, the first non-nonfunctional portion and the second non-functional portion interact to constitute the functional protein.

Illustrative Embodiments

The following Embodiments are illustrative and should not be interpreted to limit the scope of the claimed subject matter.

Embodiment 1. An engineered red blood cell comprising: (a) a first exogenous extracellular sensor; the first extracellular sensor comprising: (i) a first extracellular ligand binding domain (LBD1), (ii) a transmembrane domain (TM1), and (iii) an intracellular first fragment of a functional protein (FP1), and (b) a second exogenous extracellular sensor; the second extracellular sensor comprising: (i) a second extracellular ligand binding domain (LBD2), (ii) a transmembrane domain (TM2), and (iii) an intracellular second fragment of the functional protein (FP2); wherein: the first extracellular ligand binding domain of the first exogenous sensor and the second extracellular ligand binding domain of the second exogenous sensor bind to the same ligand to form a ternary complex, and the first fragment of the functional protein and the second fragment of the functional protein interact in the ternary complex to reconstitute functional activity of the functional protein (i.e., the ligand comprises binding sites for LBD1 and LBD2). Optionally, TM1 and TM2 may be the same or different and or may comprise a native amino acid sequence of a RBC membrane protein and/or a mutated amino acid sequence of a RBC membrane protein (e.g., where the native amino acid sequence forms multimers and the mutated amino acid sequence does not form multimers). Optionally, where FP1 comprises a N-terminal portion of a full-length functional protein and FP2 comprises a C-terminal portion of a full-length functional protein or where FP1 comprises a C-terminal portion of a full-length functional protein and FP2 comprises a N-terminal portion of a full-length functional protein.

Embodiment 2. The engineered red blood cell of embodiment 1, wherein the functional protein is a fluorescent protein (e.g., a split fluorescent protein) and the fluorescent protein emits fluorescence when the ternary complex is formed and the first fragment of the fluorescent protein and the second fragment of the fluorescent protein interact to reconstitute the fluorescent protein.

Embodiment 3. The engineered red blood cell of embodiment 2, wherein the fluorescent protein is selected from the group consisting of green fluorescent protein (GFP), EGFP (enhanced green fluorescent protein), Emerald, Superfolder GFP, Azami Green, mWasabi, TagGFP, TurboGFP, AcGFP, ZsGreen, T-Sapphire, GFP-S65T, frGFP, sfGFP, EBFP, EBFP2, Azurite, mTagBFP, ECFP, mECFP, Cerulean, mTurquoise, CyPet, AmCyan1, Midori-Ishi Cyan, TagCFP, mTFP1 (Teal), Dronpa, EYFP, Topaz, Venus, mCitrine, YPet, TagYFP, PhiYFP, ZsYellow1, mBanana, Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, mRuby, mApple, mStrawberry, AsRed2, mRFP1, JRed, mCherry, mKate, HcRed1, mRaspberry, dKeima-Tandem, HcRed-Tandem, mPlum, and AQ143.

Embodiment 4. The engineered red blood cell of any of the foregoing embodiments, wherein the first extracellular ligand binding domain (LBD1) and the transmembrane domain of the first exogenous extracellular sensor (TM1) are linked by a 5-25 amino acid linking sequence of amino acids selected from glycine, serine, and combination thereof (e.g., LBD1-GGGSGGGS-TM1; SEQ ID NO: 4); and/or wherein the transmembrane domain (TM1) and the intracellular first fragment of the functional protein of the first exogenous extracellular sensor (FP1) are linked by a 5-25 amino acid linking sequence of amino acids selected from glycine, serine, and combination thereof (e.g., TM1-GGGSGGGS-FP1; SEQ ID NO: 4).

Embodiment 5. The engineered red blood cell of any of the foregoing embodiments, wherein the second extracellular ligand binding domain (LBD2) and the transmembrane domain of the second exogenous extracellular sensor (TM2) are linked by a 5-25 amino acid linking sequence of amino acids selected from glycine, serine, and combination thereof (e.g., LBD2-GGGSGGGS-TM2; SEQ ID NO: 4); and/or wherein the transmembrane domain TM2 and the intracellular first fragment of the functional protein of the second exogenous extracellular sensor (FP2) are linked by a 5-25 amino acid linking sequence of amino acids selected from glycine, serine, and combination thereof (e.g., TM2-GGGSGGGS-FP2; SEQ ID NO: 4).

Embodiment 6. The engineered red blood cell of any of the foregoing embodiments, wherein the functional protein is an enzyme and the enzyme exhibits enzymatic activity emits when the ternary complex is formed and the first fragment of the fluorescent protein and the second fragment of the enzyme interact to reconstitute the enzyme.

Embodiment 7. The engineered red blood cell of embodiment 6, wherein the enzyme is a luciferase.

Embodiment 8. A combination of expression cassettes for preparing an engineered red blood cell, the combination comprising: (a) a first cassette expressing a first exogenous extracellular sensor; the first extracellular sensor comprising: (i) a first extracellular ligand binding domain (LBD1), (ii) a transmembrane domain (TM1), and (iii) an intracellular first fragment of a functional protein (FP1), and (b) a second cassette expressing a second exogenous extracellular sensor; the second extracellular sensor comprising: (i) a second extracellular ligand binding domain (LBD2), (ii) a transmembrane domain (TM2), and (iii) an intracellular second fragment of the functional protein (FP2); wherein: the first extracellular ligand binding domain of the first exogenous sensor and the second extracellular ligand binding domain of the second exogenous sensor bind to the same ligand to form a ternary complex, and the first fragment of the functional protein and the second fragment of the functional protein interact in the ternary complex to reconstitute functional activity of the functional protein (i.e., the ligand comprises binding sites for LBD1 and LBD2). Optionally, TM1 and TM2 may be the same or different and or may comprise a native amino acid sequence of a RBC membrane protein and/or a mutated amino acid sequence of a RBC membrane protein (e.g., where the native amino acid sequence forms multimers and the mutated amino acid sequence does not form multimers). Optionally, FP1 comprises an N-terminal portion of a full-length functional protein and FP2 comprises a C-terminal portion of a full-length functional protein or where FP1 comprises a C-terminal portion of a full-length functional protein and FP2 comprises an N-terminal portion of a full-length functional protein.

Embodiment 9. The combination of embodiment 8, wherein the expression cassettes are present on separate vectors.

Embodiment 10. The combination of embodiment 8, wherein the expression cassettes are present on the same vector.

Embodiment 11. The combination of any of the foregoing embodiments, wherein the functional protein is a fluorescent protein (e.g., a split fluorescent protein) and the fluorescent protein emits fluorescence when the ternary complex is formed and the first fragment of the fluorescent protein and the second fragment of the fluorescent protein interact to reconstitute the fluorescent protein.

Embodiment 12. The combination of embodiment 11, wherein the fluorescent protein is selected from the group consisting of green fluorescent protein (GFP), EGFP, Emerald, Superfolder GFP, Azami Green, mWasabi, TagGFP, TurboGFP, AcGFP, ZsGreen, T-Sapphire, GFP-S65T, frGFP, sfGFP, EBFP, EBFP2, Azurite, mTagBFP, ECFP, mECFP, Cerulean, mTurquoise, CyPet, AmCyan1, Midori-Ishi Cyan, TagCFP, mTFP1 (Teal), Dronpa, EYFP, Topaz, Venus, mCitrine, YPet, TagYFP, PhiYFP, ZsYellow1, mBanana, Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, mRuby, mApple, mStrawberry, AsRed2, mRFP1, JRed, mCherry, mKate, HcRed1, mRaspberry, dKeima-Tandem, HcRed-Tandem, mPlum, and AQ143.

Embodiment 13. The combination of any of the foregoing embodiments, wherein the first extracellular ligand binding domain (LBD1) and the transmembrane domain of the first exogenous extracellular sensor (TM1) are linked by a 5-25 amino acid linking sequence of amino acids selected from glycine, serine, and combination thereof (e.g., LBD1-GGGSGGGS-TM1; SEQ ID NO: 4); and/or wherein the transmembrane domain (TM1) and the intracellular first fragment of the functional protein of the first exogenous extracellular sensor (FP1) are linked by a 5-25 amino acid linking sequence of amino acids selected from glycine, serine, and combination thereof (e.g., TM1-GGGSGGGS-FP1; SEQ ID NO: 4).

Embodiment 14. The combination of any of the foregoing embodiments, wherein the second extracellular ligand binding domain (LBD2) and the transmembrane domain of the second exogenous extracellular sensor (TM2) are linked by a 5-25 amino acid linking sequence of amino acids selected from glycine, serine, and combination thereof (e.g., LBD2-GGGSGGGS-TM2; SEQ ID NO: 4); and/or wherein the transmembrane domain TM2 and the intracellular first fragment of the functional protein of the second exogenous extracellular sensor (FP2) are linked by a 5-25 amino acid linking sequence of amino acids selected from glycine, serine, and combination thereof (e.g., TM2-GGGSGGGS-FP2; SEQ ID NO: 4).

Embodiment 15. The combination of any of the foregoing embodiments, wherein the functional protein is an enzyme and the enzyme exhibits enzymatic activity emits when the ternary complex is formed and the first fragment of the fluorescent protein and the second fragment of the enzyme interact to reconstitute the enzyme.

Embodiment 16. The combination of embodiment 15, wherein the enzyme is a luciferase.

Embodiment 17. A method for detecting a ligand (or a metabolite), the method comprising contacting the engineered red blood cell of any of embodiments 1-7 with the ligand (or metabolite), and detecting functional activity of the functional protein.

Embodiment 18. The method of embodiment 17, wherein the functional protein is a fluorescent protein and detecting functional activity comprises detecting fluorescence.

Embodiment 19. The method of embodiment 17, wherein the functional protein is a luciferase protein and detecting functional activity comprises contacting the engineered red blood cell with a substrate for the luciferase protein and detecting light emitted from the engineered red blood cell.

Embodiment 20. A method for preparing the engineered red blood cells of any of embodiments 1-7, the method comprising: (I) transfecting a precursor red blood cell with a combination of expression cassettes of any of embodiments 8-16; and (II) inducing the transfected precursor red blood cell precursor cell to differentiate into a red blood cell, thereby preparing the engineered red blood cell.

Embodiment 21. A precursor red blood cell transfected with the cassettes of any of embodiments 8-16.

Embodiment 22. The engineered red blood cells of any of embodiments 1-7, wherein the first exogenous extracellular sensor and/or the second exogenous extracellular sensor comprise an amino acid sequence of a native membrane protein of red blood cells or a portion or fragment thereof (e.g., at least a portion of the transmembrane amino acid sequence of a native membrane protein of red blood cells, optionally at least a portion of the extracellular amino acid sequence of a native membrane protein of red blood cells, and optionally at least a portion of the intracellular amino acid sequence of a native membrane protein of red blood cells).

Embodiment 23. The combination of expression cassettes of any of claims 8-16, wherein the first exogenous extracellular sensor and/or the second exogenous extracellular sensor comprise an amino acid sequence of a native membrane protein of red blood cells or a portion or fragment thereof (e.g., at least a portion of the transmembrane amino acid sequence of a native membrane protein of red blood cells, optionally at least a portion of the extracellular amino acid sequence of a native membrane protein of red blood cells, and optionally at least a portion of the intracellular amino acid sequence of a native membrane protein of red blood cells).

Embodiment 24. The method of any of embodiments 17-20, wherein the first exogenous extracellular sensor and/or the second exogenous extracellular sensor comprise an amino acid sequence of a native membrane protein of red blood cells or a portion or fragment thereof (e.g., at least a portion of the transmembrane amino acid sequence of a native membrane protein of red blood cells, optionally at least a portion of the extracellular amino acid sequence of a native membrane protein of red blood cells, and optionally at least a portion of the intracellular amino acid sequence of a native membrane protein of red blood cells).

Embodiment 25. The precursor red blood cell of embodiment 21, wherein the first exogenous extracellular sensor and/or the second exogenous extracellular sensor comprise an amino acid sequence of a native membrane protein of red blood cells or a portion or fragment thereof (e.g., at least a portion of the transmembrane amino acid sequence of a native membrane protein of red blood cells, optionally at least a portion of the extracellular amino acid sequence of a native membrane protein of red blood cells, and optionally at least a portion of the intracellular amino acid sequence of a native membrane protein of red blood cells).

EXAMPLES

The following Examples are illustrative and should not be interpreted to limit the scope of the claimed subject matter.

Example 1

Abstract

Cell-based therapies comprise a blossoming, multi-billion dollar industry addressing markets ranging from cancer to autoimmune disease. An emerging frontier is the use of red blood cells (RBC), which have exceptionally long circulation times (up to 120 days—far longer than synthetic vehicles), lack DNA (and thus are safe), and can be loaded with drugs, proteins, or other cargo. Technologies that enable one to engineer RBCs to perform specific functions in vivo could serve unmet diagnostic and therapeutic needs. This invention comprises a technology for generating engineered RBC (eRBC) to serve as long-lived biosensors. Each eRBC would emit a fluorescent readout when bound to the analyte of interest, such that eRBC state could be monitored non-invasively using established technologies for fluorescent imaging (e.g., fluorescent imaging of the retina).

Applications

Applications for the disclosed technology may include, but are not limited to: (a) Diagnostics: using simple imaging technology, a patient could perform regular self-analysis and enable real-time, high frequency monitoring outside clinical settings, none of which is possible with existing technologies requiring specialized equipment, trained personnel, and/or sample collection; (b) Exposure monitoring: by a similar approach, military personal and first responders could determine whether or not they have been exposed to a potential infectious agent via monitoring output from a tailored eRBC; and (c) Basic science: eRBC could provide a facile approach to non-invasively monitoring soluble species in the serum of experimental animals.

Advantages

Advantages of the disclosed technology may include, but are not limited to: (a) eRBC are longer-lived than any injectable particle or small molecule; a single injection could enable monitoring for weeks or months; (b) eRBC biosensor output is amenable to noninvasive monitoring, without requiring sample collection, complicated analysis, or trained personnel; (c) the disclosed protein biosensors are readily customized to detect novel analytes—all that is needed is replacing the ligand binding domain with binding proteins (e.g., single chain antibodies) that bind the analyte of interest; and (c) RBC have been engineered for other applications but this represents the first technology enabling the engineering of eRBC to serve as biosensors for a range of analytes found in the blood.

Brief Summary of the Technology

This technology comprises a protein biosensor platform for engineering RBCs such that sensing of an extracellular analyte results in the reconstitution of a split functional protein in the RBC cytosol. The biosensor comprises two protein chains, each of which includes an extracellular ligand binding domain, a membrane-spanning domain, and an intracellular domain comprising half of a split functional protein (FIG. 1). In the proposed mechanism, upon binding of the ligand to the ligand binding domains, the two chains dimerize, bringing the two split protein halves into proximity causing the split functional protein to reconstitute and therefore exhibit functionality. Suitable functional proteins may include, but are not limited to, fluorescent proteins and enzymatic proteins.

In FIG. 1, each biosensor is composed of two protein chains each with an extracellular ligand binding domain (LBD1 and LBD2, respectively) and a single transmembrane pass domain (TM1 and TM2, respectively). The intracellular portion of the receptors contains one half of a split fluorescent protein (FP1 and FP2, respectively). Upon ligand binding, the two chains dimerize, allowing to two split protein halves to come into contact and reconstitute the fluorescent protein and then emit fluorescence.

Technical Description

As an initial proof of concept, we developed a receptor with extracellular ligand binding domains that heterodimerize upon binding the small molecule rapamycin (FRB and FKBP form a heterodimer in the presence of rapamycin) (FIG. 1) (for a review of the FKBP-Rapamycin-FRB ternary complex, see Banaszynski, et al., J. Am. Chem. Soc. (JACS) Articles, Mar. 9, 2005, 127, 4715-4721, the content of which is incorporate herein by reference in its entirety). In this preliminary work, we used split GFP (sGFP) as the split fluorescent protein [Ghosh 2000], although the eventual application of this technology in vivo would probably utilize reconstitution of a split infrared fluorescent protein [Filonov 2013] or split luciferase [Dixon 2016]. Our initial constructs utilized a simple single-pass transmembrane domain, and none of these receptors exhibited ligand-inducible reconstitution of GFP (FIG. 2).

Figure 2:
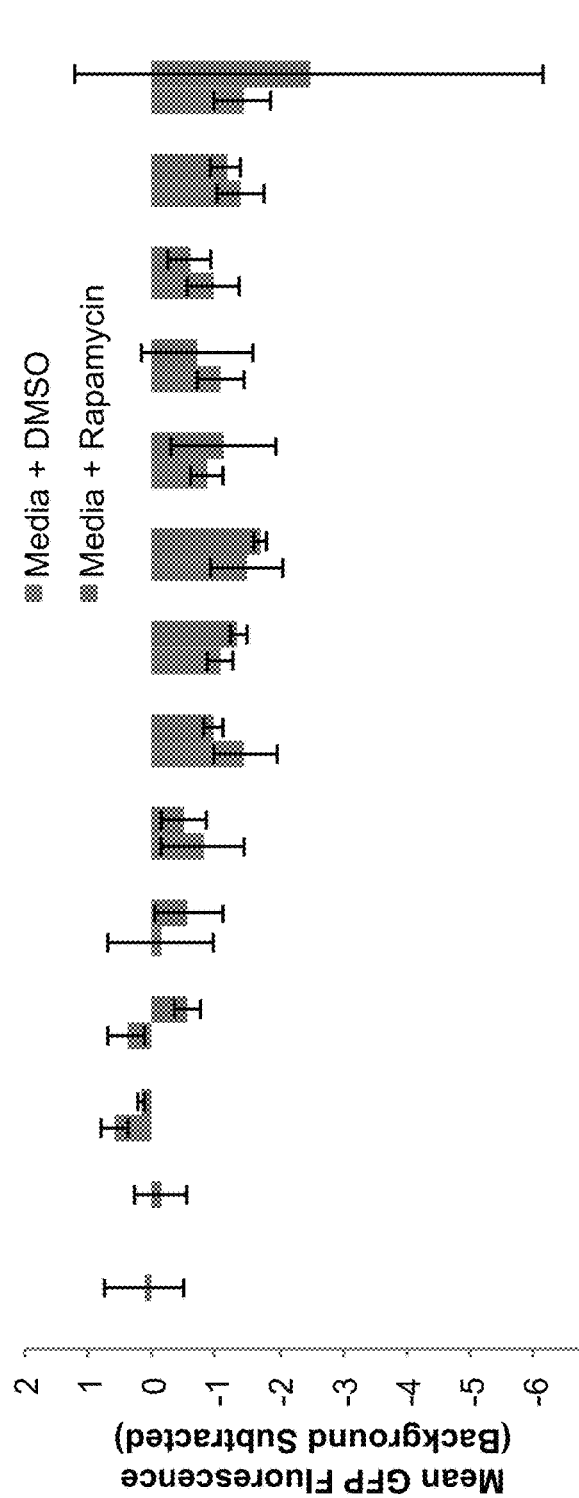
FIG. 2: Evaluation of first-generation biosensor proteins containing a simple transmembrane domain. All samples were analyzed in biological triplicate, the mean was subtracted from the mean of negative control cells (expressing only one receptor chain), and error bars represent one standard deviation. Abbreviations: RBD: Rapamycin Binding Domain—FRB or FKBP; sGFP: split GFP—GS (small fragment) or GL (large fragment)

The results in FIG. 2 represent experiments in which a library of receptors encoding a rapamycin binding domain, transmembrane domain, and split GFP half was created and transfected in pair-wise combinations into HEK293FT cells. The background signaling was very low, with most cells actually showing GFP values at or below that of the control cells (transfected with only one receptor chain). Furthermore, no combination of receptors, regardless of linker length, showed any induction of GFP upon addition of rapamycin. All transfections were performed using the $CaCl_2$-HEPES buffered saline methodology. Sixteen (16) hours post transfection, rapamycin was added with media change, and the cells were allowed to incubate for an additional 24 hours. Cells were harvested and analyzed by flow cytometry.

Figure 3:
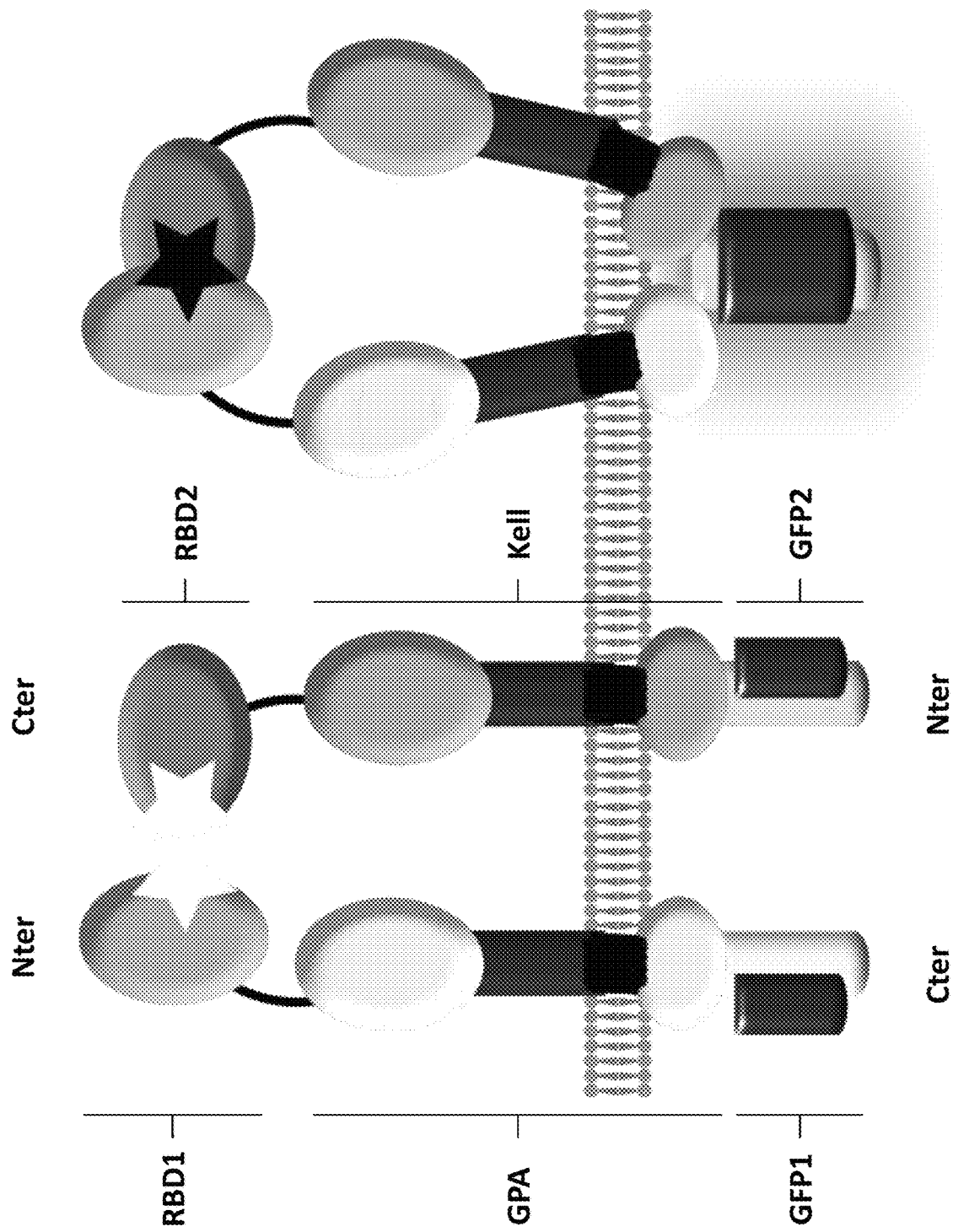
FIG. 3: Proposed mechanism of Kell-based biosensor protein and GPA-based biosensor protein. Kell and GPA, two native RBC proteins, were modified to contain extracellular rapamycin-binding domains and intracellular split GFP halves.

We next investigated whether biosensors could be constructed by fusing ligand-binding and sGFP domains to the RBC-resident proteins Kell and Glycophorin A (GPA) (FIG. 3). Kell and GPA are expressed in RBC even when expressed as genetic fusion constructs [Shi 2014]. Moreover, since GPA is a Type I membrane protein and Kell is a Type II membrane protein (Kell and GPA are expressed in opposite orientation relative to the plasma membrane), we hypothesized that fusion of sGFP fragments to the intracellular terminus of each protein may bring the sGFP fragments together in the antiparallel orientation required for reconstitution of GFP. As illustrated in FIG. 3, Kell and GPA were modified to contain extracellular rapamycin-binding domains (RBD1 and RBD2 at their extracellular N-terminus and extracellular C-terminus, respectively) and intracellular split GFP halves (GFP1 and GFP2 at their intracellular C-terminus and intracellular C-terminus, respectively). Upon the addition of rapamycin, these two protein chains can dimerize, allowing for the reconstitution of GFP. These two proteins are naturally antiparallel to one another: Kell possesses an extracellular C-terminus, and GPA an extracellular N-terminus.

Figure 4:
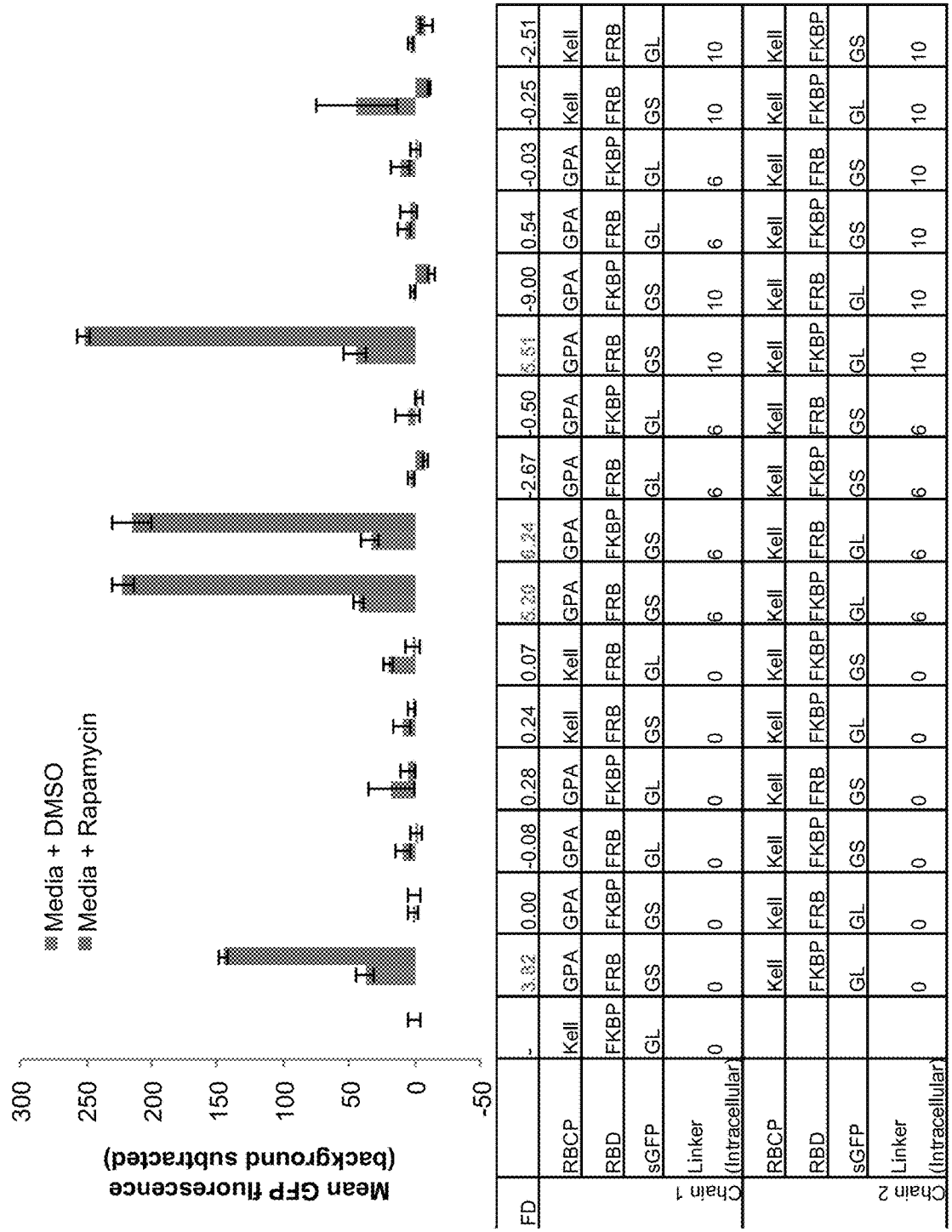
FIG. 4: Evaluation of Kell-based biosensor protein and GPA-based biosensor protein. All samples were analyzed in biological triplicate, the mean was subtracted from the mean of cells transfected with only one receptor half, and error bars represent one standard deviation. Abbreviations: RBD: Rapamycin Binding Domain—FRB or FKBP; sGFP: split GFP—GS (small fragment) or GL (large fragment); RBC: Red Blood Cell Protein.

Several of these second-generation biosensors exhibited ligand-inducible reconstitution of fluorescence (FIG. 4). Because only some combinations of receptor designs conferred ligand-inducible reconstitution, we hypothesized that geometric constraints may limit reconstitution in these receptors. Thus, we introduced longer linkers into the intracellular portions of these functional receptors (i.e., glycine-serine linkers between the transmembrane domain portion and functional protein portion of the sensors), and we observed that ligand-induced reconstitution was indeed dramatically improved (FIG. 4).

The results in FIG. 4 represent experiments in which pairs of receptors were expressed in HEK 293FT cells. These data indicate that split protein reconstitution on a membrane is feasible, given that the receptors achieve the necessary orientation for protein reconstitution. All transfections were performed using the $CaCl_2$-HEPES buffered saline methodology. Sixteen (16) hours post-transfection, rapamycin was added along with media change, and cells were incubated for an additional 24 hours before being harvested and analyzed by flow cytometry.

Figure 5:
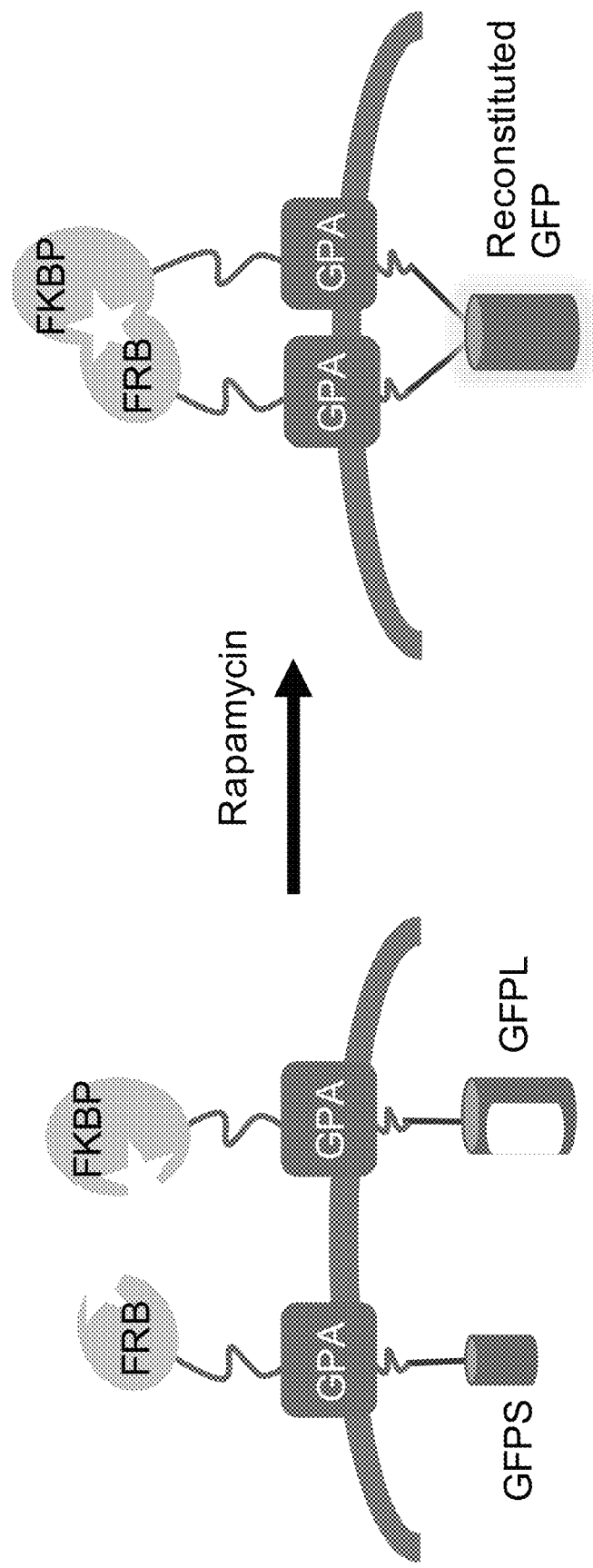
FIG. 5: Proposed mechanism of GPA only-based biosensor proteins.

These initial experiments demonstrated that RBC-resident proteins may be engineered into ligand-inducible biosensor proteins, and that such proteins may be iteratively improved using design-driven approaches. These data also support the feasibility of adapting this modular receptor design to incorporate novel ligand binding domains and novel fluorophore outputs Because GPA is known to be expressed at higher levels than is Kell, we also investigated GPA-only biosensors (FIG. 5). As illustrated in FIG. 5, GPA, a native RBC protein, was modified to create two sensors (i.e., two fusion proteins) having extracellular rapamycin-binding domains (FRB or FKBP) and intracellular split GFP halves (GFPS and GFPL). Upon the addition of rapamycin, these two protein chains can dimerize, allowing for the reconstitution of GFP. These biosensors also conferred ligand-inducible reconstitution of sGFP (FIG. 6).

Figure 6:
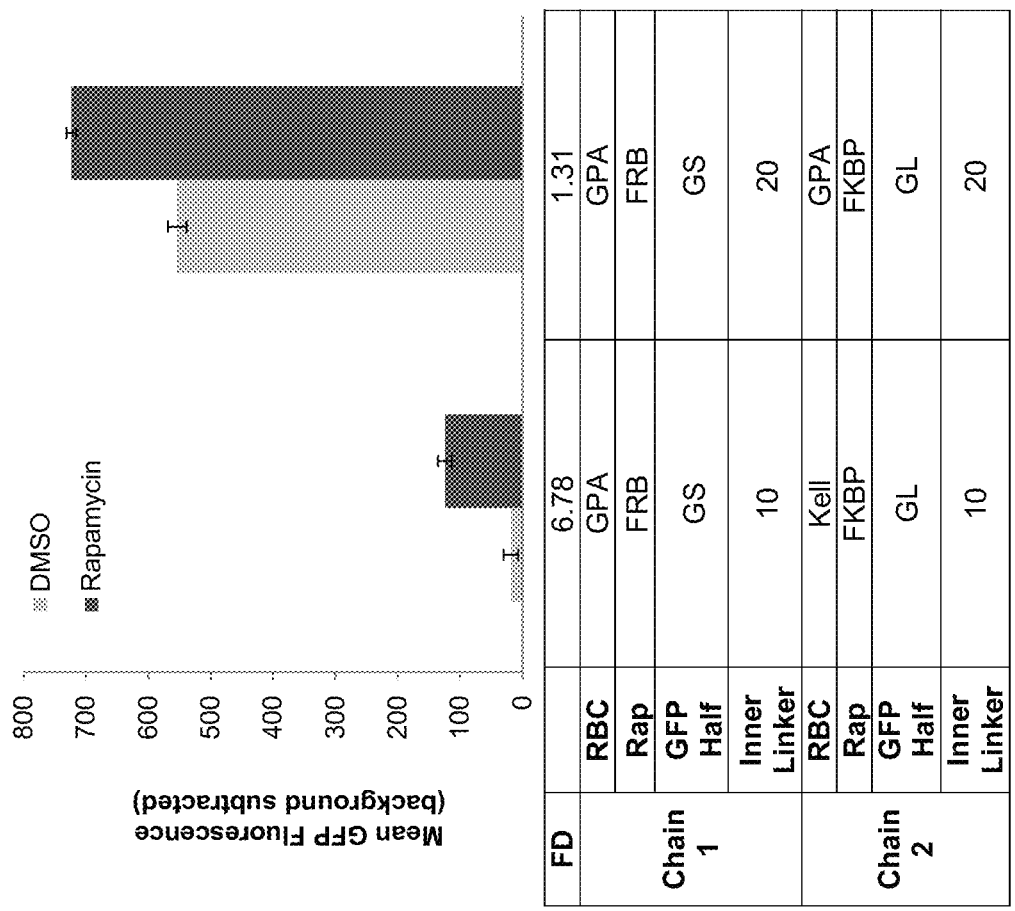
FIG. 6: Evaluation of GPA only-based biosensor proteins compared to GPA-based and Kell-based biosensor proteins. All samples were analyzed in biological triplicate, the background auto-fluorescence of the cells with only the color control was subtracted off, and error bars represent one standard deviation. Abbreviations: Rap: Rapamycin Binding Domain—FRB or FKBP; GFP Half: split GFP—GS (small fragment) or GL (large fragment); RBC: Red Blood Cell Protein.

The results in FIG. 6 represent experiments in which pairs of receptors were expressed in HEK 293FT cells. All transfections were performed using the $CaCl_2$-HEPES buffered saline methodology. Sixteen (16) hours post-transfection, rapamycin was added along with media change, and cells were incubated for an additional 24 hours before being harvested and analyzed by flow cytometry.

Figure 7:
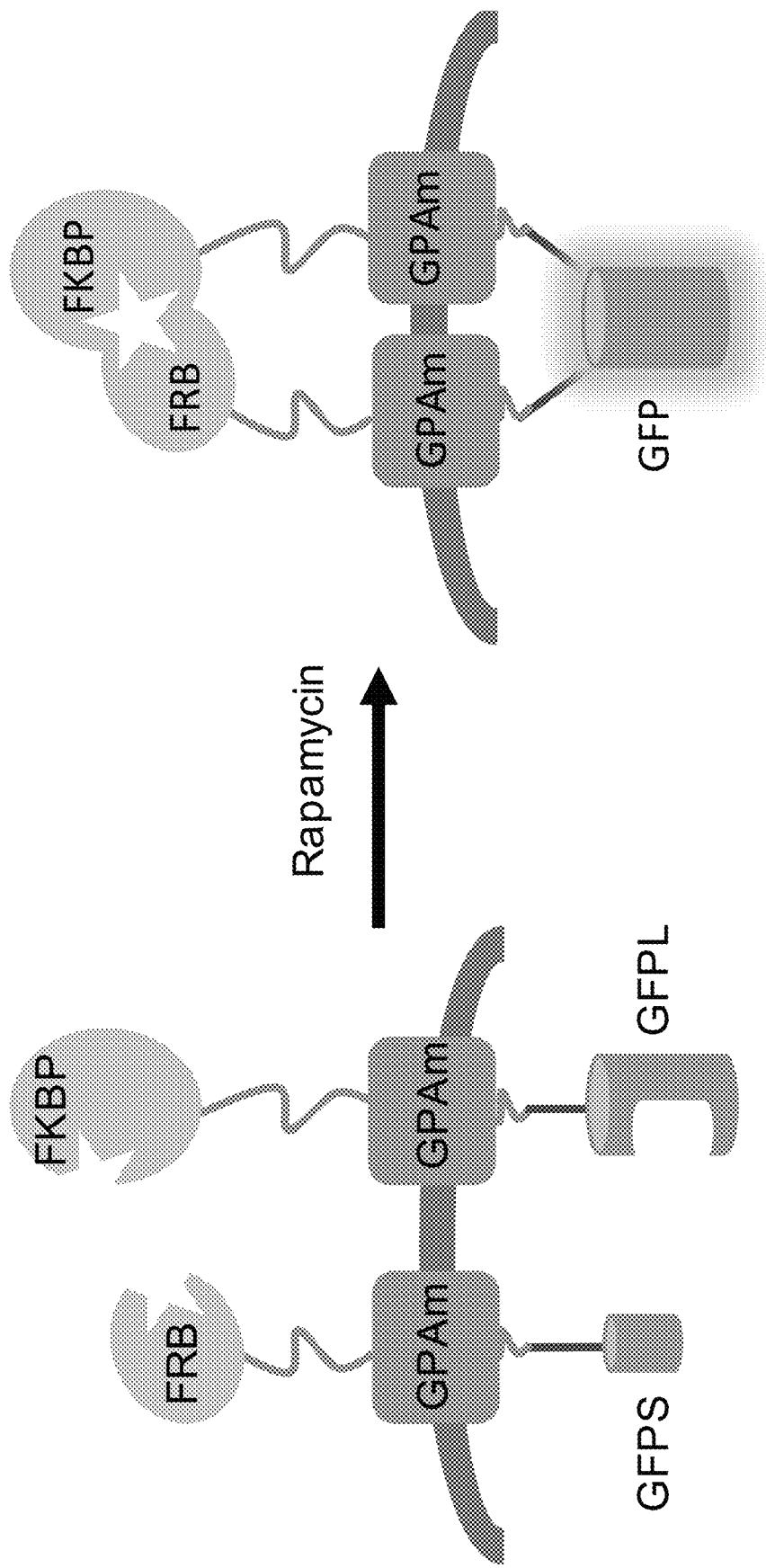
FIG. 7: Second generation proposed mechanism of mutated GPA (GPAm)-based biosensor proteins. Abbreviations: Rap: Rapamycin Binding Domain—FRB or FKBP; GFP Half: split GFP—GS (small fragment) or GL (large fragment); RBC: Red Blood Cell Protein.
Figure 8:
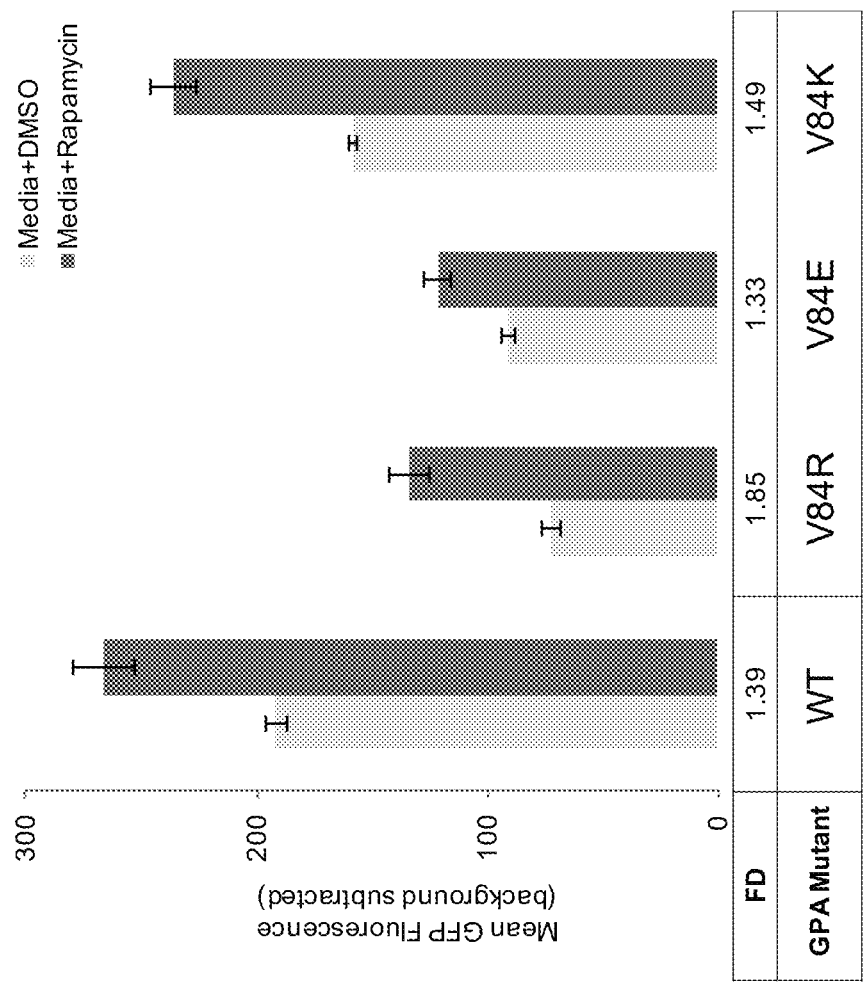
FIG. 8: Mutation-driven improvement of eRBC biosensors. All samples were analyzed in biological triplicate, the mean was subtracted from the mean of negative control cells, and error bars represent one standard deviation. Abbreviations: FD: fold-difference; GPA Mutant: WT: Wild Type, V84R: Valine 84 to Arginine, V84E: Valine 84 to Glutamic Acid, V84K: Valine 84 to Lysine.
Figure 9:
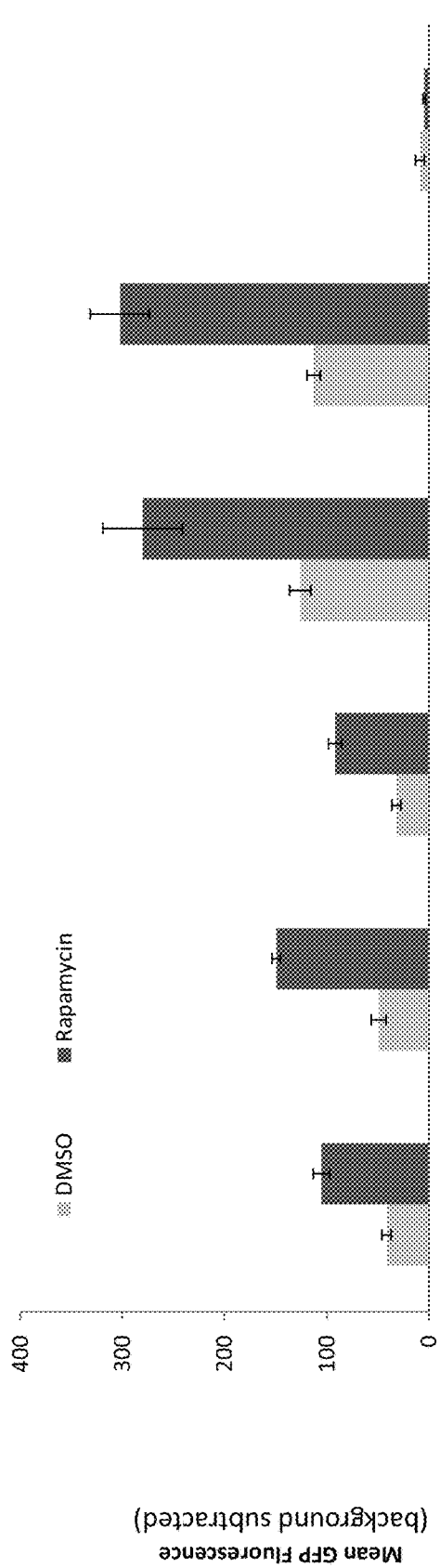
FIG. 9: Evaluation of mutated GPA-based biosensor proteins compared to GPA-based and Kell-based biosensor proteins. All samples were analyzed in biological triplicate, error bars represent one standard deviation. Abbreviations: Rap: Rapamycin Binding Domain—FRB or FKBP; GFP Half: split GFP—GS (small fragment) or GL (large fragment); RBC: Red Blood Cell Protein; Mutate: X—wild type or V84R: Valine 84 to Arginine mutation.

We hypothesized that biosensors based upon wild-type GPA exhibited high background signaling due to homodimerization in the absence of ligand, and therefore we investigated biosensors in which one or both GPA domains required for homodimerization were mutated to reduce homodimerization in the absence of ligand (FIG. 7). As illustrated in FIGS. 7-9, biosensor proteins described in FIG. 6 were modified to mutate the transmembrane domain of GPA to decrease native background dimerization. As illustrated in FIG. 7 and FIG. 8, GPA was mutated in the transmembrane domain (GPAm) by converting the neutral valine at position 84 to a charged amino acid (V84R: Valine 84 to Arginine, V84E: Valine 84 to Glutamic Acid, V84K: Valine 84 to Lysine), and GPA was modified to contain N-terminal extracellular rapamycin-binding domains (FRB or FKBP) and C-terminal intracellular split GFP halves (GFPS or GFPL). Upon the addition of rapamycin, these two protein chains can dimerize, allowing for the reconstitution of GFP.

The mutated proteins then were expressed in HEK293FT cells to test dimerization in the presence of rapamycin. (See FIG. 8 and FIG. 9). The results in FIG. 8 and FIG. 9 represent experiments in which pairs of receptors were expressed in HEK 293FT cells. All transfections were performed using the $CaCl_2$-HEPES buffered saline methodology. Sixteen (16) hours post-transfection, rapamycin was added along with media change, and cells were incubated for an additional 24 hours before being harvested and analyzed by flow cytometry. As observed, the mutated biosensors exhibited sGFP reconstitution that was lower that that exhibited by wild-type GPA based receptors but higher than that exhibited by Kell-based biosensors (FIG. 8 and FIG. 9).

Figure 10:
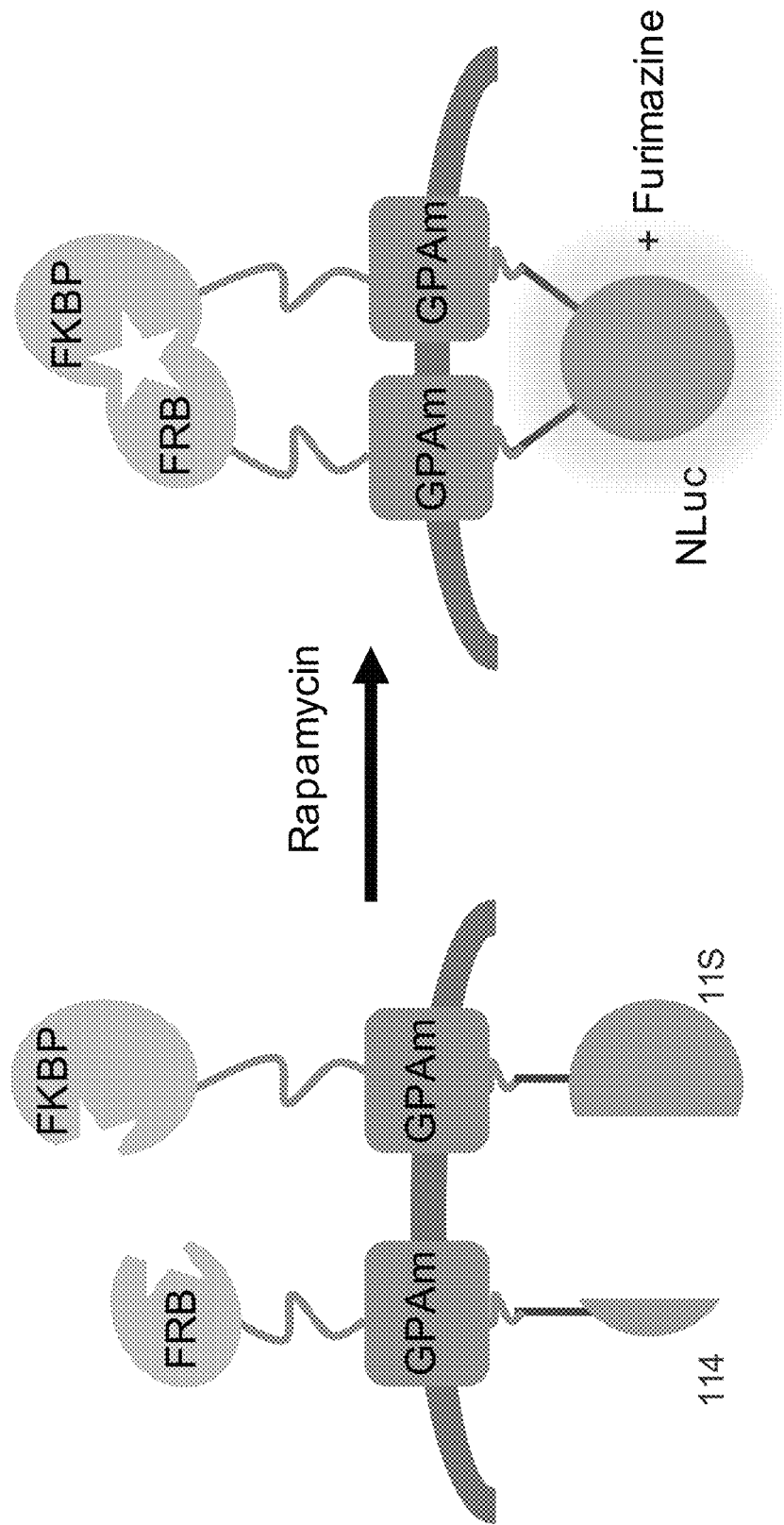
FIG. 10: Third generation proposed mechanism of mutated GPA-based biosensor proteins.

Because sGFP reconstitution efficiency may be limited by parameters not directly related to the eRBC biosensor mechanism, we also investigated whether we could generate a biosensor based upon reconstitution of a different signaling domain—split NANOLUCIFERASE™ [Dixon 2016](FIG. 10). As illustrated in FIG. 10, GPA was mutated in the transmembrane domain (GPAm, see FIGS. 7-9) and was modified to contain N-terminal extracellular rapamycin-binding domains (FRB or FKBP) and C-terminal intracellular split NANOLUCIFERASE™ halves (114 and 11S). Upon the addition of rapamycin, these two protein chains can dimerize, allowing for the reconstitution of NANOLUCIFERASE™, and luminescence upon addition of the substrate, furimazine.

Figure 11:
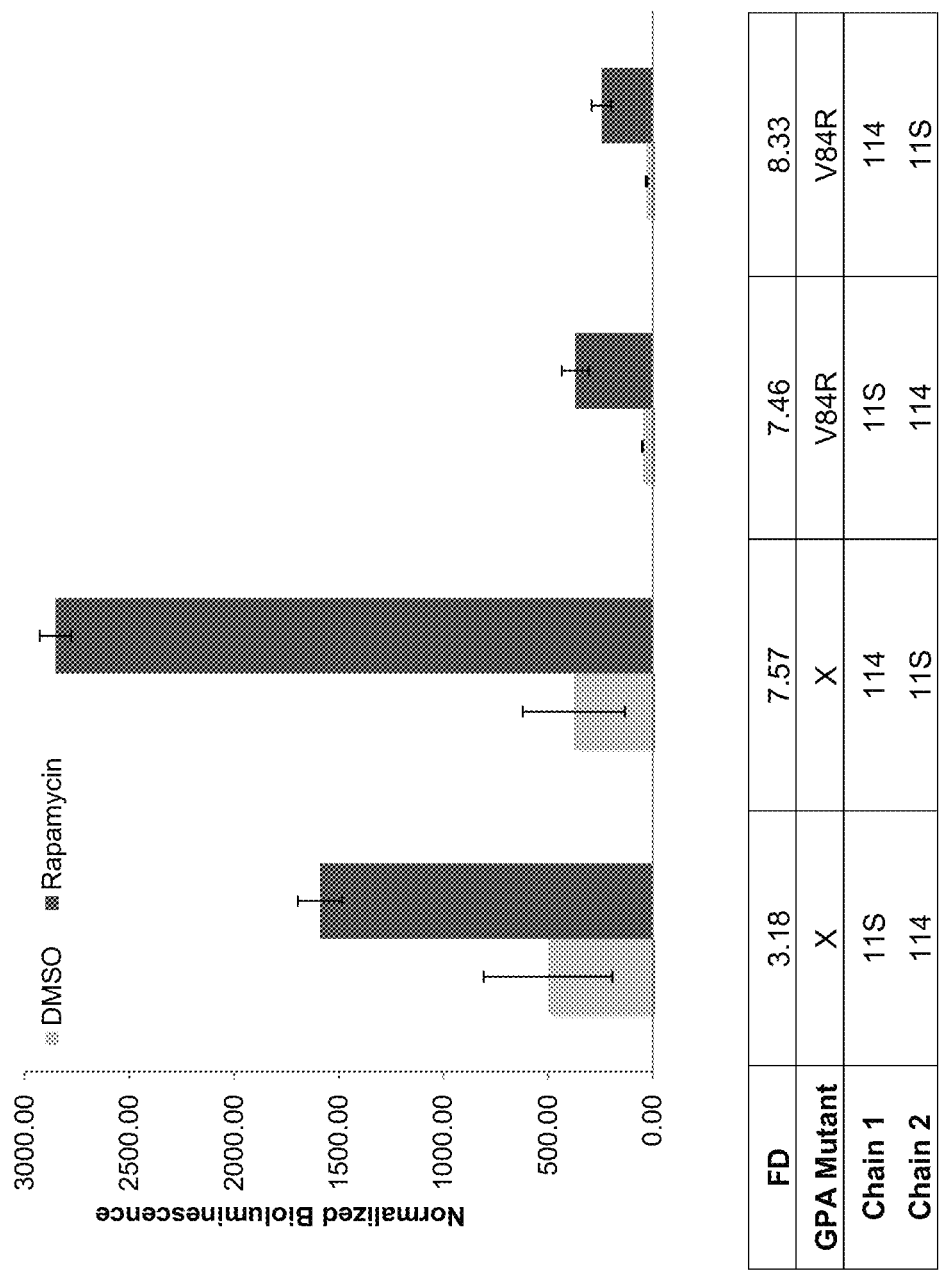
FIG. 11: Evaluation of GPA-based biosensor proteins compared to mutated GPA-based biosensor proteins with NANOLUCIFERASE™ output. All samples were analyzed in biological triplicate, error bars represent one standard deviation. Abbreviations: GPA mutant—X: wild type GPA, V84R: Valine 84 to Arginine; NANOLUCIFERASE™ Half—11S (larger half) or 114 (smaller half); FD—fold difference.

These NANOLUCIFERASE™-based biosensors exhibited robust ligand-inducible reconstitution of luciferase activity, when expressed in IHEK293FT cells (FIG. 11). The results in FIG. 11 represent experiments in which pairs of receptors were expressed in HEK 293FT cells. All transfections were performed using the $CaCl_2$-HEPES buffered saline methodology. Sixteen (16) hours post-transfection, rapamycin was added along with media change, and cells were incubated for an additional 24 hours before being harvested and analyzed by plate reader for luciferase luminescence.

Figure 12:
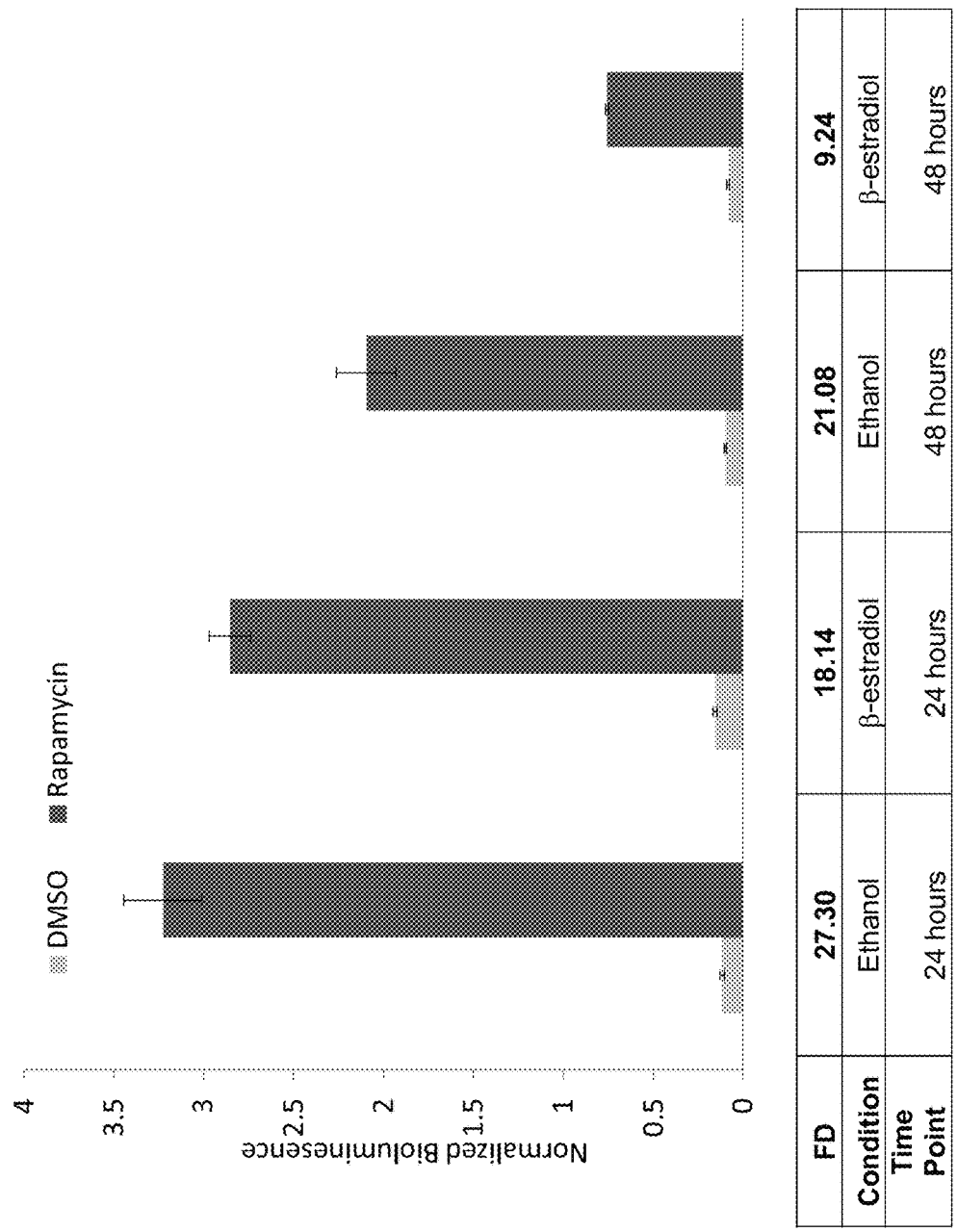
FIG. 12: Evaluation of GPA-based biosensor proteins with NANOLUCIFERASE™ output in Gler cells, which approximate red blood cells. Abbreviations: FD—fold difference.

To test whether such eRBC biosensors would be expressed in functional in red blood cells (erythrocytes), we next expressed our biosensors in Gler cells. Gler cells can be induced to differentiate into erythrocytes by exposure to beta-estradiol. We observed that our biosensors were highly functional in Gler cells, without or without differentiation stimuli, and when differentiated for various lengths of time (FIG. 12). As illustrated in FIG. 12, Gler cells were spinoculated with retrovirus containing pairs of receptors and GFP expressed in one plasmid. Cells were sorted for GFP expression. GFP+ cells received either ethanol or -estradiol (to drive differentiation into an erythrocyte phenotype) and either DMSO or rapamycin. Cell lysates were collected in passive lysis buffer 24 hours and 48 hours after receiving treatment. Technical replicates of cell lysates were analyzed for GFP fluorescence on a plate reader. Then a luciferase assay was performed on the cell lysates with the addition of substrate. Abbreviations: FD—fold difference. These results indicate that our eRBC biosensors are expressed, retained, and functional in erythrocytes, validating the core concept described in this disclosure.

Figure 13:
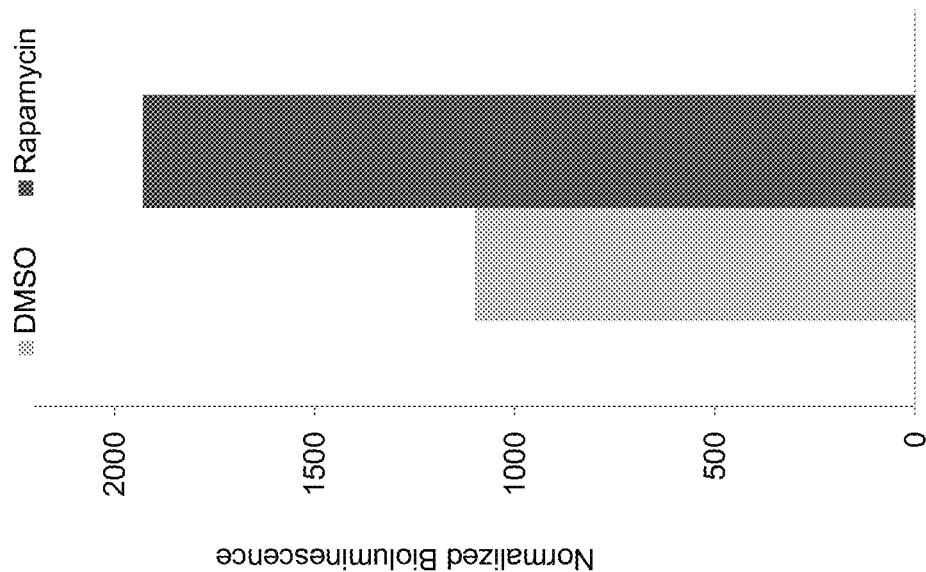
FIG. 13: Evaluation of GPA-based biosensor proteins with NANOLUCIFERASE™ output in human CD34+ cells.

We also tested the biosensors in human CD34+ cells. The results in FIG. 13 represent experiments in which human CD34+ cells were spinoculated with a lentiviral vector expressing a pair of receptors and Puromycin resistance. Cells were selected with Puromycin and then differentiated for 14 days. Differentiated cells received either DMSO or rapamycin. One hour after treatment, cell lysates were collected in passive lysis buffer. A luciferase assay was performed on cell lysates.

REFERENCES

Shi, J. H. et al. Engineered red blood cells as carriers for systemic delivery of a wide array of functional probes. Proceedings of the National Academy of Sciences of the United States of America 111, 10131-10136, doi:DOI 10.1073/pnas.1409861111 (2014).

Ghosh, I., Hamilton, A. D. & Regan, L. Antiparallel leucine zipper-directed protein reassembly: Application to the green fluorescent protein. J Am Chem Soc 122, 5658-5659, doi:Doi 10.1021/Ja994421w (2000).

Filonov, G. S., Verkhusha, V. V. A Near-Infrared BiFC Reporter for In Vivo Imaging of Protein-Protein Interactions. Chemistry & Biology 20, 1078-1086 (2013).

Daringer, N; Dudek, R; Schwarz, K; Leonard, J. A Modular Extracellular Sensor Architecture for Engineering Mammalian Cell-based Devices. ACS Synthetic Biology, 3 (12), 892-902 (2014).

Dixon, A. S., et al. Nantou Complementation Reporter Optimized for Accurate Measurement of Protein Interactions in Cells. ACS Chem Biol 11(2) 400-408, doi: DOI 10.1021/acschembio.5b00753 (2016).

Li, E., et al. Transmembrane helix dimerization: beyond the search for sequence motifs. Biochim Biophys Acta 1818 (2): 183-193 (2012).

Lemmon, M. A., et al. Glycophorin A dimerization is driven by specific interactions between transmembrane alpha-helices. J Biol Chem 267(11): 7683-7689 (1992).

Example 2

Reference is made to the Abstract entitled "Engineering Red Blood Cell-Based Biosensors for Physiological Monitoring," Authors: Dolberg, T. B., Schwarz, K. A., Leonard, J. M. which was presented at the 2016 Synthetic Biology: Engineering, Evolution & Design (SEED) conference on Jul. 19, 2016, and which Abstract is incorporated by reference herein in its entirety.

Cell-based therapies have a wide range of applications ranging from cancer immunotherapy to regenerative medicine. A promising emerging frontier of this field is the development of engineered red blood cells (eRBCs) for therapeutic and diagnostic applications. RBCs have exceptionally long circulation times (around 40 days—far longer than synthetic vehicles), lack DNA (and thus are safe), and can be loaded with drugs, proteins, or other cargo. Technologies that enable one to engineer RBCs to perform specific functions in vivo could serve unmet diagnostic and therapeutic needs. In particular, new technologies are required for non-invasive, routine monitoring for pathogen exposure (e.g., in the context of first responders) and for "actionable" analytes (e.g., markers of inflammation post-surgery).

In this project, we sought to develop eRBC biosensors than detect highly toxic agents, with the long-term goal of enabling one to detect exposure to these agents prior to the onset of physical symptoms. As a first step towards this goal, we designed and evaluated a novel biosensor strategy that is suitable to achieving biosensing in eRBCs, which lack DNA and thus require a readout other than gene expression. Towards this end, we engineered a novel cell-surface receptor protein in which ligand binding induces receptor dimerization, which then facilitates reconstitution of an intracellular split fluorescent protein. Ultimately, eRBC fluorescence may be monitored noninvasively using established technologies for fluorescent imaging of the retina. Importantly, our strategy involves modification of RBC-resident proteins, since retention of membrane proteins during RBC maturation is a tightly regulated and an incompletely understood process. In this study, we comparatively evaluated a range of biosensor architectures that implement the proposed mechanism, identified design biosensor features that successfully conferred significant ligand-induced generation of fluorescent output, and investigated strategies for improving biosensor performance (e.g., minimization of background fluorescence and enhancing fold-induction upon exposure to ligand). This crucial proof-of-principle demonstration establishes a foundation for developing eRBC biosensors that could ultimately address an unmet need for noninvasive monitoring of physiological signals for a range of diagnostic applications.

Example 3

Reference is made to the Abstract entitled "Engineering Red Blood Cell-Based Biosensors for Physiological Monitoring," Authors: Dolberg, T. B., Schwarz, K. A., Leonard, J. M., which was presented at the 2016 annual conference of the American Institute of Chemical Engineers (AIChE) on Nov. 14, 2016 and which Abstract is incorporated by reference herein in its entirety.

Cell-based therapies have a wide range of applications ranging from cancer immunotherapy to regenerative medicine. A promising emerging frontier of this field is the development of engineered red blood cells (eRBCs) for therapeutic and diagnostic applications. RBCs have exceptionally long circulation times (around 120 days—far longer than synthetic vehicles), lack DNA (and thus are safe), and can be loaded with drugs, proteins, or other cargo. Technologies that enable one to engineer RBCs to act as biosensors, performing specific functions in vivo, could serve unmet diagnostic and therapeutic needs. In particular, new technologies are required for non-invasive, routine monitoring for pathogen exposure (e.g., in the context of first responders) and for other "actionable" analytes (e.g., markers of inflammation post-surgery).

In this project, we are developing eRBC biosensors that generate a fluorescent output upon detection of the analyte of interest. Ultimately, eRBC biosensor fluorescent output may be monitored non-invasively using established technologies for fluorescent imaging of the retina. Using this simple imaging technology, a patient could perform regular self-analysis and enable real time, high frequency monitoring outside clinical settings, none of which is possible with existing technologies requiring specialized equipment, trained personnel, and/or sample collection. Thus, such biosensors that enable the detection of actionable analytes could benefit exposed personnel by accelerating the initiation of treatment (perhaps before obvious symptoms present) and reduction of further exposure risks when possible.

As a first step towards the goal of building eRBC biosensors, we designed and evaluated a novel biosensor strategy that is suitable for achieving biosensing in eRBCs, which lack DNA and thus require a readout other than gene expression. Towards this end, we engineered a novel cell-surface receptor protein in which ligand binding induces receptor dimerization, which then facilitates reconstitution of an intracellular split fluorescent protein. Importantly, our strategy involves modification of RBC-resident proteins, since retention of membrane proteins during RBC maturation is a tightly regulated and an incompletely understood process. We comparatively evaluated a range of biosensor architectures that implement the proposed mechanism, enabling us to identify biosensor designs and design features that successfully conferred significant ligand-induced generation of fluorescent output. We also evaluated and implemented strategies for improving biosensor performance, including minimization of background fluorescence and enhancing fold-induction upon exposure to ligand. This crucial proof-of-principle demonstration establishes a foundation for developing eRBC biosensors that could ultimately address an unmet need for non-invasive monitoring of physiological signals for a range of diagnostic applications.

Example 4

Reference is made to the Abstract entitled "Engineering Red Blood Cell-Based Biosensors for Physiological Monitoring," Authors: Dolberg, T. B., Schwarz, K. A., Leonard, J. M.," which is to be presented at the 2017 Midwest Regional Conference (MRC) of the American Institute of Chemical Engineers (AIChE) on Mar. 1, 2017 and which Abstract is incorporated by reference herein in its entirety.

Cell-based therapies have a wide range of applications ranging from cancer immunotherapy to regenerative medicine. A promising emerging frontier of this field is the development of engineered red blood cells (eRBCs) for therapeutic and diagnostic applications. RBCs are an attractive platform for diagnostics because they have exceptionally long circulation times (around 120 days—far longer than synthetic vehicles), lack DNA (and thus are safe), and can be loaded with drugs, proteins, or other cargo. Recent technological advances have enabled the large-scale production of RBCs from precursor cells, which may potentially be harnessed to generate off-the shelf eRBC-based products to meet medical needs, including both diagnostic and therapeutic applications.

The specific goal of this project is to generate eRBC-based technologies enabling noninvasive monitoring for pathogen exposure (e.g., in the context of first responders) and for other "actionable" analytes (e.g., markers of inflammation post-surgery). Towards this goal, we are developing eRBC biosensors that generate a fluorescent output upon detection of the analyte of interest, and this output may be monitored non-invasively using established technologies for fluorescent imaging of the retina. These biosensors would enable the detection of actionable analytes thus benefitting exposed personnel by accelerating the initiation of treatment (perhaps before obvious symptoms present) and reducing of further exposure risks when possible.

As a first step to enable RBCs to act as sensors, we designed and evaluated a novel biosensor strategy that is suitable for achieving biosensing in eRBCs, which lack DNA and thus require a readout other than gene expression. Towards this end, we engineered a novel cell-surface receptor protein in which ligand binding induces receptor dimerization, which then facilitates reconstitution of an intracellular split fluorescent protein. Importantly, our strategy involves modification of RBC-resident proteins, since retention of membrane proteins during RBC maturation is a tightly regulated and an incompletely understood process. We comparatively evaluated a range of biosensor architectures that implement the proposed mechanism, enabling us to identify biosensor designs and design features that successfully conferred significant ligand-induced generation of fluorescent output. We also evaluated and implemented strategies for improving biosensor performance, including minimization of background fluorescence and enhancing fold-induction upon exposure to ligand. This crucial proof-of-principle demonstration establishes a foundation for developing eRBC biosensors that could ultimately address an unmet need for non-invasive monitoring of physiological signals for a range of diagnostic applications.

Example 5

Reference is made to U.S. Publication No. 2014-0234851, published on Aug. 21, 2014, which discloses modular extracellular sensor architecture (MESA) for cell-based biosensors, and which is incorporated herein by reference in its entirety. The modular exogenous extracellular sensor architecture disclosed in U.S. Publication No. 2014-0234851 may be adapted for use in the engineered red blood cell-based biosensors disclosed and contemplated herein.

Example 6

Background. This example describes how engineered mammalian biosensor technology can be applied to RBC-based technologies. The MESA family of engineered cell-surface biosensors (see, e.g., U.S. Publication No. 2014-0234851) enables the transduction of an extracellular ligand-binding event into a change in intracellular state. Of particular relevance to engineering RBCs, this intracellular state change can comprise reconstitution of a split protein, which may be an enzyme (as demonstrated using a split TEV protease) or potentially another functional domain (e.g., a split fluorescent protein). Briefly summarized below are several potential applications for engineering high value RBC using such technologies.

Pathogen exposure monitoring. RBCs could be engineered to monitor exposure to a pathogen and provide a readout that is easily monitored. A target pathogen could be dengue virus, for which serial exposure to multiple serotypes significantly increases risk for developing severe hemorrhagic symptoms. Thus, using engineered RBCs (eRBCs) to monitor patients or warfighters for secondary exposure could trigger rapid intervention to reduce morbidity or mortality. The biosensor readout could be reconstitution of a split fluorescent protein (e.g., an infrared fluorescent protein (IFP) that is spectrally distinguishable from hemoglobin in RBC), and eRBC fluorescence could be monitored using a technique similar to fluorescent angiography of the retina. Such eRBCs could also incorporate a second fluorophore to enable quantitative normalization of biosensor readout. Distinct biosensors could be engineered to provide pathogen or serotype-specific biosensing. Alternatively, biosensor readout could comprise reconstitution of a bioluminescent catalyst (e.g., luciferase or another enzyme, for example that catalyzes production of a product that yields a color change in excreted urine) and/or eRBC biosensor state could be evaluated ex vivo using a blood sample.

Physiological monitoring. Using techniques similar to those described above, eRBC biosensors could be used to monitor blood concentrations of physiologically-important species over time using noninvasive techniques. Potential targets include (a) Low-density lipoprotein (LDL), certain forms of which promote immuno-inflammatory processes and drive atherosclerosis, which could be useful for evaluating or tracking cholesterol levels or (b) cytokines that predict the onset of acute transplant rejection, such as IL-6, which may predict acute kidney transplant rejection.

Incorporation of MESA-type biosensors into eRBCs. Because only a subset of proteins is retained in mature RBC, MESA-type biosensors may be redesigned to coopt localization of retained proteins such as glycophorin or Kell. Potential strategies include non-covalent tethering via the introduction of protein-protein interaction domains into both MESA proteins and glycophorin and/or Kell.

Induction of immune tolerance. Although expression of non-native protein domains on the surface of eRBC may enable immunological clearance of eRBCs, some evidence indicates that expression of proteins in or on RBC promotes active induction of immunological tolerance.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A biosensor expressed in a blood cell, comprising:
   (a) a first protein comprising:
      (i) a first extracellular ligand binding domain,
      (ii) a first transmembrane domain comprising a portion of an amino acid sequence from a red blood cell native membrane protein,
      (iii) an intracellular first fragment of a functional protein, and
      (iv) an amino acid linker connecting the first transmembrane domain and the intracellular first fragment of the functional protein; and
   (b) a second protein comprising:
      (i) a second extracellular ligand binding domain,
      (ii) a second transmembrane domain,
      (iii) an intracellular second fragment of the functional protein, and
      (iv) an amino acid linker connecting the second transmembrane domain and the intracellular second fragment of the functional protein;
   wherein the first extracellular ligand binding domain and the second extracellular ligand binding domain bind to the same ligand, wherein the first fragment of the functional protein and the second fragment of the functional protein are capable of interacting to reconstitute activity of the functional protein, and wherein the amino acid linker of the first protein or the amino acid linker of the second protein comprises 7-25 amino acids.

2. The biosensor of claim 1, wherein the amino acid linker of the first protein and the amino acid linker of the second protein each comprise 7-25 amino acids.

3. The biosensor of claim 1, wherein the amino acid linker of the first protein and the amino acid linker of the second protein each comprise a sequence of amino acids selected from glycine, serine, and combinations thereof.

4. The biosensor of claim 1, wherein the amino acid linker of the first protein and the amino acid linker of the second protein each comprise the sequence GGGSGGGS (SEQ ID NO: 4).

5. The biosensor of claim 1, wherein the functional protein is a fluorescent protein and the fluorescent protein emits fluorescence when the ternary complex is formed and the first fragment of the fluorescent protein and the second fragment of the fluorescent protein interact to reconstitute the fluorescent protein.

6. The biosensor of claim 5, wherein the fluorescent protein is selected from the group consisting of green fluorescent protein (GFP), EGFP, Emerald, Superfolder GFP, Azami Green, mWasabi, TagGFP, TurboGFP, AcGFP, ZsGreen, T-Sapphire, GFP-S65T, frGFP, sfGFP, EBFP, EBFP2, Azurite, mTagBFP, ECFP, mECFP, Cerulean, mTurquoise, CyPet, AmCyan1, Midori-Ishi Cyan, TagCFP, mTFP1 (Teal), Dronpa, EYFP, Topaz, Venus, mCitrine, YPet, TagYFP, PhiYFP, ZsYellow1, mBanana, Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, mRuby, mApple, mStrawberry, AsRed2, mRFP1, JRed, mCherry, mKate, HcRed1, mRaspberry, dKeima-Tandem, HcRed-Tandem, mPlum, and AQ143.

7. The biosensor of claim 1, wherein the first extracellular ligand binding domain and the first transmembrane domain of the first recombinant extracellular sensor are linked by a 5-25 amino acid sequence of amino acids selected from glycine, serine, and combinations thereof.

8. The biosensor of claim 1, wherein the second extracellular ligand binding domain and the second transmembrane domain of the first recombinant extracellular sensor are linked by a 5-25 amino acid sequence of amino acids selected from glycine, serine, and combinations thereof.

9. The biosensor of claim 1, wherein the first extracellular ligand binding domain and the first transmembrane domain of the first recombinant extracellular sensor are linked by a 5-25 amino acid sequence of amino acids selected from glycine, serine, and combinations thereof; and wherein the second extracellular ligand binding domain and the second transmembrane domain of the first recombinant extracellular sensor are linked by a 5-25 amino acid sequence of amino acids selected from glycine, serine, and combinations thereof.

10. The biosensor of claim 1, wherein the functional protein is an enzyme and the enzyme exhibits enzymatic activity when the ternary complex is formed and the first fragment of the enzyme and the second fragment of the enzyme interact to reconstitute the enzyme.

11. The biosensor of claim 10, wherein the enzyme is a luciferase.

12. A combination of expression cassettes for expressing the biosensor of claim 1 in a red blood cell, the combination comprising a first expression cassette and a second expression cassette, wherein the first expression cassette encodes the first protein and a second expression cassette encodes the second protein.

13. A biosensor expressed in a blood cell, comprising:
    (a) a first protein comprising:
        (i) a first extracellular ligand binding domain,
        (ii) a first transmembrane domain comprising a portion of an amino acid sequence from a red blood cell native membrane protein,
        (iii) an extracellular linker comprising 7-25 amino acids and connecting the first extracellular ligand binding domain and the first transmembrane domain,
        (iv) an intracellular first fragment of a functional protein, and
        (v) an intracellular linker comprising 7-25 amino acids and connecting the first transmembrane domain and the intracellular first fragment of the functional protein; and
    (b) a second protein comprising:
        (i) a second extracellular ligand binding domain,
        (ii) a second transmembrane domain,
        (iii) an extracellular linker comprising 7-25 amino acids and connecting the second extracellular ligand binding domain and the second transmembrane domain,
        (iv) an intracellular second fragment of a functional protein, and
        (v) an intracellular linker comprising 7-25 amino acids and connecting the second transmembrane domain and the intracellular second fragment of the functional protein;
wherein the first extracellular ligand binding domain and the second extracellular ligand binding domain bind to the same ligand, wherein the first fragment of the functional protein and the second fragment of the functional protein are capable of interacting to reconstitute activity of the functional protein, and wherein linkers comprise a sequence of amino acids selected from glycine, serine, and combinations thereof.

14. The biosensor of claim 13, wherein the intracellular linkers each comprise the sequence GGGSGGGS (SEQ ID NO: 4).

15. The biosensor of claim 13, wherein the functional protein is a fluorescent protein and the fluorescent protein emits fluorescence when the ternary complex is formed and the first fragment of the fluorescent protein and the second fragment of the fluorescent protein interact to reconstitute the fluorescent protein.

16. The biosensor of claim 15, wherein the fluorescent protein is selected from the group consisting of green fluorescent protein (GFP), EGFP, Emerald, Superfolder GFP, Azami Green, mWasabi, TagGFP, TurboGFP, AcGFP, ZsGreen, T-Sapphire, GFP-S65T, frGFP, sfGFP, EBFP, EBFP2, Azurite, mTagBFP, ECFP, mECFP, Cerulean, mTurquoise, CyPet, AmCyan1, Midori-Ishi Cyan, TagCFP, mTFP1 (Teal), Dronpa, EYFP, Topaz, Venus, mCitrine, YPet, TagYFP, PhiYFP, ZsYellow1, mBanana, Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, mRuby, mApple, mStrawberry, AsRed2, mRFP1, JRed, mCherry, mKate, HcRed1, mRaspberry, dKeima-Tandem, HcRed-Tandem, mPlum, and AQ143.

17. The biosensor of claim 13, wherein the functional protein is an enzyme and the enzyme exhibits enzymatic activity when the ternary complex is formed and the first fragment of the enzyme and the second fragment of the enzyme interact to reconstitute the enzyme.

18. The biosensor of claim 17, wherein the enzyme is a luciferase.

19. A combination of expression cassettes for expressing the biosensor of claim 13 in a red blood cell, the combination comprising a first expression cassette and a second expression cassette, wherein the first expression cassette encodes the first protein and a second expression cassette encodes the second protein.

* * * * *

SEQUENCE LISTING

```
<160> NUMBER OF SEQ ID NOS: 4

<210> SEQ ID NO 1
<211> LENGTH: 150
<212> TYPE: PRT
<213> ORGANISM: Homo sapiens

<400> SEQUENCE: 1

Met Tyr Gly Lys Ile Ile Phe Val Leu Leu Leu Ser Glu Ile Val Ser
1               5                   10                  15

Ile Ser Ala Leu Ser Thr Thr Glu Val Ala Met His Thr Ser Thr Ser
            20                  25                  30

Ser Ser Val Thr Lys Ser Tyr Ile Ser Ser Gln Thr Asn Asp Thr His
        35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Glu Thr Gly Glu Arg
65                  70                  75                  80

Val Gln Leu Ala His His Phe Ser Glu Pro Glu Ile Thr Leu Ile Ile
                85                  90                  95

Phe Gly Val Met Ala Gly Val Ile Gly Thr Ile Leu Leu Ile Ser Tyr
            100                 105                 110

Gly Ile Arg Arg Leu Ile Lys Lys Ser Pro Ser Asp Val Lys Pro Leu
        115                 120                 125

Pro Ser Pro Asp Thr Asp Val Pro Leu Ser Ser Val Glu Ile Glu Asn
    130                 135                 140

Pro Glu Thr Ser Asp Gln
145                 150

<210> SEQ ID NO 2
<211> LENGTH: 732
<212> TYPE: PRT
<213> ORGANISM: Homo sapiens
```

<400> SEQUENCE: 2

Met Glu Gly Gly Asp Gln Ser Glu Glu Pro Arg Glu Arg Ser Gln
1               5                   10                  15

Ala Gly Gly Met Gly Thr Leu Trp Ser Gln Glu Ser Thr Pro Glu Glu
            20                  25                  30

Arg Leu Pro Val Glu Gly Ser Arg Pro Trp Ala Val Ala Arg Arg Val
            35                  40                  45

Leu Thr Ala Ile Leu Ile Leu Gly Leu Leu Cys Phe Ser Val Leu
50                  55                  60

Leu Phe Tyr Asn Phe Gln Asn Cys Gly Pro Arg Pro Cys Glu Thr Ser
65                  70                  75                  80

Val Cys Leu Asp Leu Arg Asp His Tyr Leu Ala Ser Gly Asn Thr Ser
                85                  90                  95

Val Ala Pro Cys Thr Asp Phe Phe Ser Phe Ala Cys Gly Arg Ala Lys
                100                 105                 110

Glu Thr Asn Asn Ser Phe Gln Glu Leu Ala Thr Lys Asn Lys Asn Arg
                115                 120                 125

Leu Arg Arg Ile Leu Glu Val Gln Asn Ser Trp His Pro Gly Ser Gly
130                 135                 140

Glu Glu Lys Ala Phe Gln Phe Tyr Asn Ser Cys Met Asp Thr Leu Ala
145                 150                 155                 160

Ile Glu Ala Ala Gly Thr Gly Pro Leu Arg Gln Val Ile Glu Glu Leu
                165                 170                 175

Gly Gly Trp Arg Ile Ser Gly Lys Trp Thr Ser Leu Asn Phe Asn Arg
                180                 185                 190

Thr Leu Arg Leu Leu Met Ser Gln Tyr Gly His Phe Pro Phe Phe Arg
                195                 200                 205

Ala Tyr Leu Gly Pro His Pro Ala Ser Pro His Thr Pro Val Ile Gln
210                 215                 220

Ile Asp Gln Pro Glu Phe Asp Val Pro Leu Lys Gln Asp Gln Glu Gln
225                 230                 235                 240

Lys Ile Tyr Ala Gln Ile Phe Arg Glu Tyr Leu Thr Tyr Leu Asn Gln
                245                 250                 255

Leu Gly Thr Leu Leu Gly Gly Asp Pro Ser Lys Val Gln Glu His Ser
                260                 265                 270

Ser Leu Ser Ile Ser Ile Thr Ser Arg Leu Phe Gln Phe Leu Arg Pro
            275                 280                 285

Leu Glu Gln Arg Arg Ala Gln Gly Lys Leu Phe Gln Met Val Thr Ile
290                 295                 300

Asp Gln Leu Lys Glu Met Ala Pro Ala Ile Asp Trp Leu Ser Cys Leu
305                 310                 315                 320

Gln Ala Thr Phe Thr Pro Met Ser Leu Ser Pro Ser Gln Ser Leu Val
                325                 330                 335

Val His Asp Val Glu Tyr Leu Lys Asn Met Ser Gln Leu Val Glu Glu
                340                 345                 350

Met Leu Leu Lys Gln Arg Asp Phe Leu Gln Ser His Met Ile Leu Gly
                355                 360                 365

Leu Val Val Thr Leu Ser Pro Ala Leu Asp Ser Gln Phe Gln Glu Ala
                370                 375                 380

Arg Arg Lys Leu Ser Gln Lys Leu Arg Glu Leu Thr Glu Gln Pro Pro
385                 390                 395                 400

Met Pro Ala Arg Pro Arg Trp Met Lys Cys Val Glu Glu Thr Gly Thr

```
                        405                 410                 415
Phe Phe Glu Pro Thr Leu Ala Ala Leu Phe Val Arg Glu Ala Phe Gly
                420                 425                 430

Pro Ser Thr Arg Ser Ala Ala Met Lys Leu Phe Thr Ala Ile Arg Asp
            435                 440                 445

Ala Leu Ile Thr Arg Leu Arg Asn Leu Pro Trp Met Asn Glu Glu Thr
        450                 455                 460

Gln Asn Met Ala Gln Asp Lys Val Ala Gln Leu Gln Val Glu Met Gly
465                 470                 475                 480

Ala Ser Glu Trp Ala Leu Lys Pro Glu Leu Ala Arg Gln Glu Tyr Asn
                485                 490                 495

Asp Ile Gln Leu Gly Ser Ser Phe Leu Gln Ser Val Leu Ser Cys Val
            500                 505                 510

Arg Ser Leu Arg Ala Arg Ile Val Gln Ser Phe Leu Gln Pro His Pro
        515                 520                 525

Gln His Arg Trp Lys Val Ser Pro Trp Asp Val Asn Ala Tyr Tyr Ser
530                 535                 540

Val Ser Asp His Val Val Phe Pro Ala Gly Leu Leu Gln Pro Pro
545                 550                 555                 560

Phe Phe His Pro Gly Tyr Pro Arg Ala Val Asn Phe Gly Ala Ala Gly
                565                 570                 575

Ser Ile Met Ala His Glu Leu Leu His Ile Phe Tyr Gln Leu Leu Leu
            580                 585                 590

Pro Gly Gly Cys Leu Ala Cys Asp Asn His Ala Leu Gln Glu Ala His
        595                 600                 605

Leu Cys Leu Lys Arg His Tyr Ala Ala Phe Pro Leu Pro Ser Arg Thr
610                 615                 620

Ser Phe Asn Asp Ser Leu Thr Phe Leu Glu Asn Ala Ala Asp Val Gly
625                 630                 635                 640

Gly Leu Ala Ile Ala Leu Gln Ala Tyr Ser Lys Arg Leu Leu Arg His
                645                 650                 655

His Gly Glu Thr Val Leu Pro Ser Leu Asp Leu Ser Pro Gln Gln Ile
            660                 665                 670

Phe Phe Arg Ser Tyr Ala Gln Val Met Cys Arg Lys Pro Ser Pro Gln
        675                 680                 685

Asp Ser His Asp Thr His Ser Pro Pro His Leu Arg Val His Gly Pro
690                 695                 700

Leu Ser Ser Thr Pro Ala Phe Ala Arg Tyr Phe Arg Cys Ala Arg Gly
705                 710                 715                 720

Ala Leu Leu Asn Pro Ser Ser Arg Cys Gln Leu Trp
                725                 730

<210> SEQ ID NO 3
<211> LENGTH: 238
<212> TYPE: PRT
<213> ORGANISM: Aequorea victoria

<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

```
Thr Thr Gly Lys Leu Pro Val Pro Trp Pro Thr Leu Val Thr Thr Phe
    50              55              60
Ser Tyr Gly Val Gln Cys Phe Ser Arg Tyr Pro Asp His Met Lys Gln
65              70              75              80
His Asp Phe Phe Lys Ser Ala Met Pro Glu Gly Tyr Val Gln Glu Arg
            85              90              95
Thr Ile Phe Phe Lys Asp Asp Gly Asn Tyr Lys Thr Arg Ala Glu Val
            100             105             110
Lys Phe Glu Gly Asp Thr Leu Val Asn Arg Ile Glu Leu Lys Gly Ile
            115             120             125
Asp Phe Lys Glu Asp Gly Asn Ile Leu Gly His Lys Leu Glu Tyr Asn
    130             135             140
Tyr Asn Ser His Asn Val Tyr Ile Met Ala Asp Lys Gln Lys Asn Gly
145             150             155             160
Ile Lys Val Asn Phe Lys Ile Arg His Asn Ile Glu Asp Gly Ser Val
                165             170             175
Gln Leu Ala Asp His Tyr Gln Gln Asn Thr Pro Ile Gly Asp Gly Pro
            180             185             190
Val Leu Leu Pro Asp Asn His Tyr Leu Ser Thr Gln Ser Ala Leu Ser
        195             200             205
Lys Asp Pro Asn Glu Lys Arg Asp His Met Val Leu Leu Glu Phe Val
    210             215             220
Thr Ala Ala Gly Ile Thr His Gly Met Asp Glu Leu Tyr Lys
225             230             235

<210> SEQ ID NO 4
<211> LENGTH: 8
<212> TYPE: PRT
<213> ORGANISM: Homo sapiens

<400> SEQUENCE: 4

Gly Gly Gly Ser Gly Gly Gly Ser
1               5
```